United States Patent
Larsen et al.

(10) Patent No.: US 9,597,086 B2
(45) Date of Patent: Mar. 21, 2017

(54) OCCLUSIVE DEVICES

(71) Applicant: W. L. Gore & Associates, Inc., Newark, DE (US)

(72) Inventors: Coby C. Larsen, Flagstaff, AZ (US); Steven J. Masters, Flagstaff, AZ (US); Edward E. Shaw, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 237 days.

(21) Appl. No.: 14/479,093

(22) Filed: Sep. 5, 2014

(65) Prior Publication Data

US 2014/0379019 A1 Dec. 25, 2014

Related U.S. Application Data

(63) Continuation of application No. 13/615,228, filed on Sep. 13, 2012.

(Continued)

(51) Int. Cl.
*A61M 29/00* (2006.01)
*A61B 17/12* (2006.01)
*A61B 17/00* (2006.01)

(52) U.S. Cl.
CPC ...... *A61B 17/1215* (2013.01); *A61B 17/0057* (2013.01); *A61B 17/12122* (2013.01); *A61B 17/12145* (2013.01); *A61B 17/12113* (2013.01); *A61B 2017/00243* (2013.01); *A61B 2017/00526* (2013.01); *A61B 2017/00579* (2013.01);

(Continued)

(58) Field of Classification Search
CPC .......... A61B 17/12122; A61B 17/1215; A61B 17/12145; A61B 17/12113; A61B 2017/00632; A61B 2017/00575; A61B 2017/00592; A61B 2017/00597; A61B 2017/00579; A61B 2017/00641; A61B 2017/00867

See application file for complete search history.

(56) References Cited

U.S. PATENT DOCUMENTS

| 5,217,486 A | 6/1993 | Rice et al. |
| 5,344,427 A | 9/1994 | Cottenceau et al. |

(Continued)

FOREIGN PATENT DOCUMENTS

| EP | 2481381 | 8/2012 |
| JP | 2007502689 A1 | 2/2007 |

(Continued)

OTHER PUBLICATIONS

International Preliminary Report on Patentability for PCT/US2012/055537, issued Mar. 18, 2014, 10 pages.

(Continued)

*Primary Examiner* — Robert Lynch

(57) ABSTRACT

An occlusive device includes a frame element having a distal end and a proximal end, and a delivery configuration and a deployed configuration. The occlusive device also includes an occlusive face having a peripheral edge, where the occlusive face positioned toward the proximal end of the frame element. The occlusive device also includes at least one anchor positioned at the peripheral edge of the occlusive face, where the at least one anchor extends at an acute angle to the peripheral edge of the occlusive face.

24 Claims, 19 Drawing Sheets

Related U.S. Application Data

(60) Provisional application No. 61/535,830, filed on Sep. 16, 2011.

(52) U.S. Cl.
CPC .............. *A61B 2017/00592* (2013.01); *A61B 2017/00597* (2013.01); *A61B 2017/00632* (2013.01); *A61B 2017/00641* (2013.01); *A61B 2017/00867* (2013.01)

(56) References Cited

U.S. PATENT DOCUMENTS

| | | | |
|---|---|---|---|
| 5,562,726 | A | 10/1996 | Chuter |
| 5,709,704 | A | 1/1998 | Nott et al. |
| 5,713,917 | A | 2/1998 | Leonhardt et al. |
| 5,720,776 | A | 2/1998 | Chuter et al. |
| 5,725,552 | A * | 3/1998 | Kotula ............... A61B 17/0057 604/285 |
| 5,904,703 | A | 5/1999 | Gilson |
| 5,961,546 | A | 10/1999 | Robinson et al. |
| 6,013,093 | A | 1/2000 | Nott et al. |
| 6,214,025 | B1 | 4/2001 | Thistle et al. |
| 6,231,581 | B1 | 5/2001 | Shank et al. |
| 6,231,589 | B1 | 5/2001 | Wessman et al. |
| 6,273,900 | B1 | 8/2001 | Nott et al. |
| 6,322,585 | B1 | 11/2001 | Khosravi et al. |
| 6,328,727 | B1 | 12/2001 | Frazier et al. |
| 6,346,117 | B1 | 2/2002 | Greenhalgh |
| 6,451,051 | B2 | 9/2002 | Drasler et al. |
| 6,485,513 | B1 | 11/2002 | Fan |
| 6,491,704 | B2 | 12/2002 | Gifford, III et al. |
| 6,712,842 | B1 | 3/2004 | Gifford, III et al. |
| 6,746,472 | B2 | 6/2004 | Frazier et al. |
| 7,169,160 | B1 | 1/2007 | Middleman et al. |
| 7,331,992 | B2 | 2/2008 | Randall et al. |
| 7,566,336 | B2 | 7/2009 | Corcoran et al. |
| 7,572,289 | B2 | 8/2009 | Sisken et al. |
| 7,601,159 | B2 | 10/2009 | Ewers et al. |
| 7,655,034 | B2 | 2/2010 | Mitchell et al. |
| 7,815,591 | B2 | 10/2010 | Levine et al. |
| 7,846,179 | B2 | 12/2010 | Belef et al. |
| 7,887,580 | B2 | 2/2011 | Randall et al. |
| 8,029,559 | B2 | 10/2011 | Sisken et al. |
| 8,241,350 | B2 | 8/2012 | Randall et al. |
| 8,273,105 | B2 | 9/2012 | Cohen et al. |
| 8,870,947 | B2 | 10/2014 | Shaw |
| 2004/0034366 | A1 | 2/2004 | Van der Burg et al. |
| 2005/0038470 | A1 | 2/2005 | Van der Burg et al. |
| 2007/0162048 | A1 | 7/2007 | Quinn et al. |
| 2007/0270891 | A1 | 11/2007 | McGuckin |
| 2008/0147111 | A1 | 6/2008 | Johnson et al. |
| 2008/0208329 | A1 | 8/2008 | Bishop |
| 2009/0054723 | A1 | 2/2009 | Khairkhahan et al. |
| 2009/0062838 | A1 | 3/2009 | Brumleve et al. |
| 2010/0057195 | A1 | 3/2010 | Roeder et al. |
| 2011/0054515 | A1 | 3/2011 | Bridgeman et al. |
| 2012/0022638 | A1 | 1/2012 | Leewood et al. |
| 2013/0023981 | A1 | 1/2013 | Dierking et al. |
| 2013/0073029 | A1 | 3/2013 | Shaw |
| 2013/0245666 | A1 | 9/2013 | Larsen et al. |
| 2014/0012303 | A1 | 1/2014 | Heipl |
| 2015/0051695 | A1 | 2/2015 | Shaw |

FOREIGN PATENT DOCUMENTS

| | | |
|---|---|---|
| JP | 2010527742 A | 8/2010 |
| JP | 2011509117 A | 3/2011 |
| WO | 2005/072652 | 8/2005 |
| WO | 2010/024881 | 3/2010 |
| WO | 2011/031981 | 3/2011 |

OTHER PUBLICATIONS

International Preliminary Report on Patentability for PCT/US2012/055445, issued Mar. 18, 2014, 9 pages.
International Search Report & Written Opinion in International Application No. PCT/US2012/055445, mailed Dec. 5, 2012, 15 pages.
International Search Report and Written Opinion for PCT/US2012/055537, mailed Dec. 5, 2012, 5 pages.

* cited by examiner

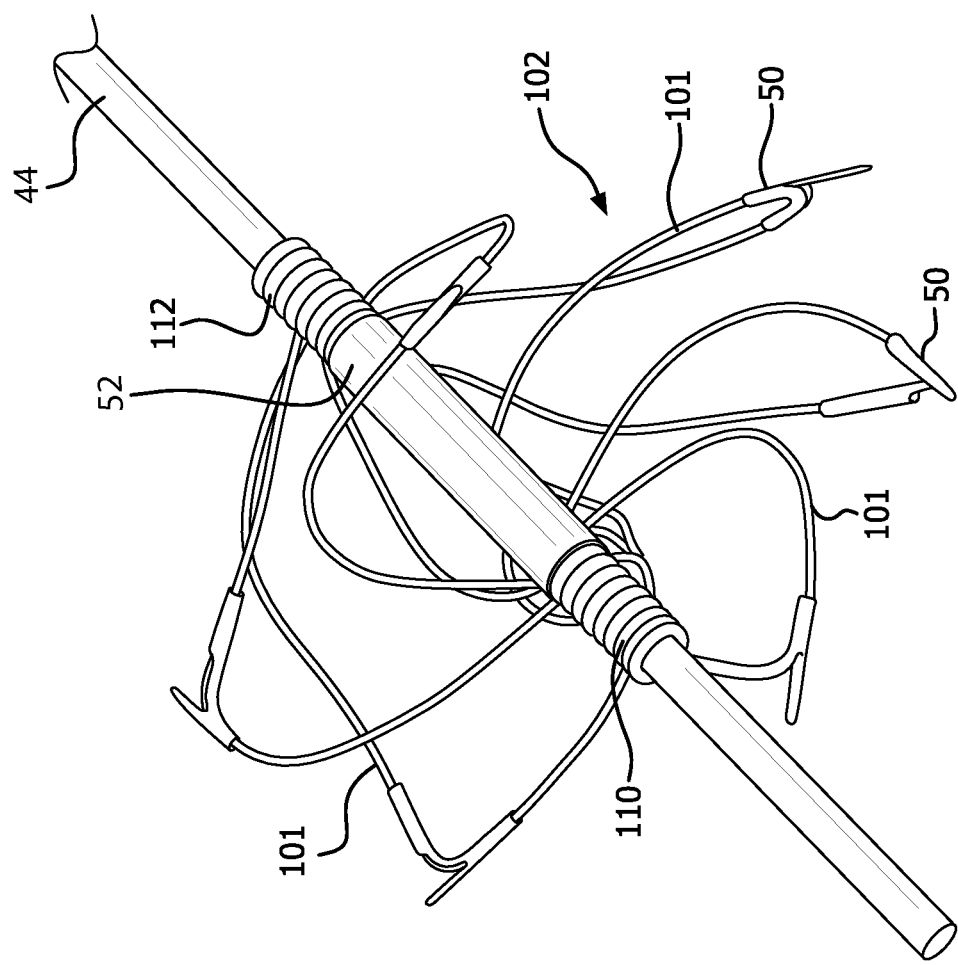

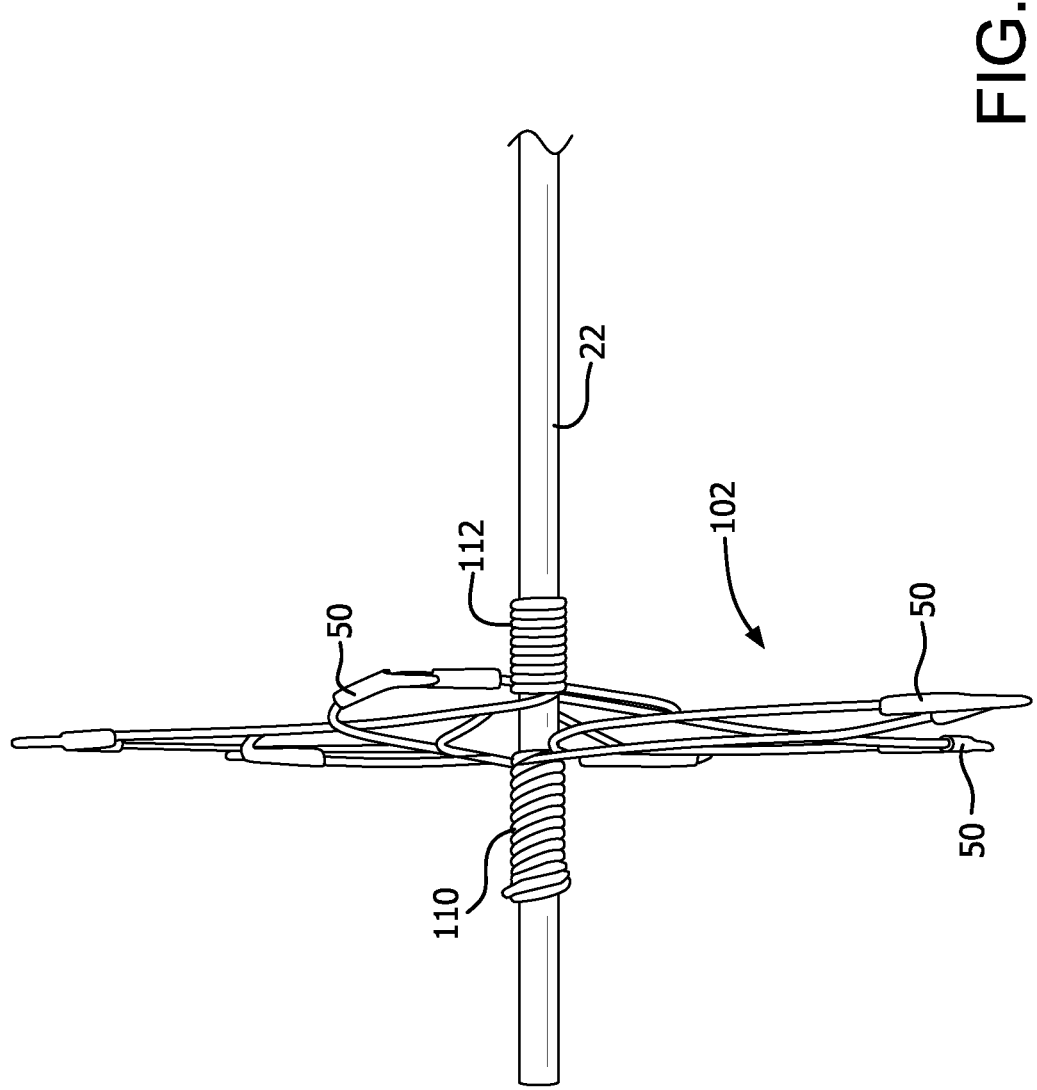

OCCLUSIVE DEVICES

TECHNOLOGY FIELD

The disclosure relates to occlusive devices useful, for example, in occluding structures or conduits within a patient, particularly an atrial appendage in the human heart, and methods of making and using the devices, including delivering, deploying, and retrieving or repositioning the devices. Devices described herein can be delivered percutaneously or in an endovascular fashion.

BACKGROUND

Embolic stroke is the nation's third leading killer, and is a major cause of disability. There are over 780,000 strokes per year in the United States alone. Of these, roughly 110,000 are hemorrhagic, and 670,000 are ischemic (either due to vessel narrowing or to embolism). The most common cause of ischemic stroke of cardiac origin is thromboemboli due to atrial fibrillation. One out of every six strokes (approximately 130,000 per year) is attributed to atrial fibrillation. Atrial fibrillation is the most common heart arrhythmia; it results in a rapid and chaotic heartbeat that lowers cardiac output and leads to irregular and turbulent blood flow in the vascular system. There are over eight million people worldwide with atrial fibrillation, with about eight hundred thousand new cases reported each year. Atrial fibrillation is associated with a greater risk of stroke compared with age-matched healthy controls. A patient with atrial fibrillation typically has a significantly decreased quality of life due, in part, to the fear of stroke, and the pharmaceutical regimen necessary to reduce that risk.

When patients develop atrial thrombus from atrial fibrillation, the clot occurs in or originates from the left atrial appendage of the heart over ninety percent of the time. The left atrial appendage is a closed cavity that looks like a small thumb or windsock; it is connected to the anterolateral wall of the left atrium between the mitral valve and the root of the left pulmonary vein. The left atrial appendage contracts with the left atrium during a normal heart cycle, thus keeping blood from becoming stagnant. However, with atrial fibrillation, the left atrial appendage often fails to contract with any vigor due to disorganized electrical signals. As a result, thrombi can be predisposed to form in the stagnant blood within the left atrial appendage.

Pharmacological therapies for stroke prevention in atrial fibrillation patients such as oral or systemic administration of warfarin have often been generally inadequate due to serious side effects and lack of patient compliance. Invasive surgical or thorascopic techniques have been used to obliterate the left atrial appendage; however, many patients are not suitable candidates for such procedures due to compromised condition or previous cardiac surgery. In addition, the perceived risks of these surgical procedures often outweigh the potential benefits.

Many of the current commercial devices that attempt to occlude the left atrial appendage for stroke prevention in atrial fibrillation patients utilize a rigid, cylindrical support frame with tissue-piercing fixation members that engage tissue in the appendage itself. The opening (ostium) of the left atrial appendage varies in geometry and size. Sealing the left atrial appendage with a rigid frame that presupposes a circular ostium may not be effective in preventing thromboemboli from entering systemic circulation.

Another concern with some of the current devices is with the filtering type membranes used by the devices. These membranes are macroporous and typically require significant periods of time to provide cessation of blood flow through the membrane. Such membranes can take hours to weeks to substantially occlude the left atrial appendage. The possibility exists for thromboemboli to enter the blood stream while the clotting/occluding process of the filtering membrane takes place. Many of these atrial fibrillation patients are on some type of blood thinning (anticoagulant or antiplatelet) medication, which could prolong the clotting/occluding process for these filtering membranes and expose patients to stroke risk.

SUMMARY

In a first general aspect, an occlusive device includes a frame element having a distal end and a proximal end, and a delivery configuration and a deployed configuration. The occlusive device also includes an occlusive face having a peripheral edge, where the occlusive face positioned toward the proximal end of the frame element. The occlusive device also includes at least one anchor positioned at the peripheral edge of the occlusive face, where the at least one anchor extends at an acute angle to the peripheral edge of the occlusive face.

In various implementations, the at least one anchor may include a tissue engagement member that protrudes in a proximal direction with reference to an axial dimension of the device. The at least one anchor may include a tissue engagement member that protrudes in a distal direction with reference to an axial dimension of the device. The at least one anchor may include a tissue engagement member that may extend tangentially from a portion of the frame element near the anchor. The at least one anchor may be located substantially within a plane defined by the peripheral edge. The occlusive face may have a concave orientation. The occlusive face may have a convex orientation. The occlusive face may have a substantially planar orientation. Multiple anchors may be disposed on the peripheral edge. The frame may include a tapered region. The occlusive device may also include a membrane configured to inhibit passage of blood, where the membrane covers at least a portion of the frame. The membrane may include a fluoropolymer. The membrane may include polytetrafluoroethylene. The membrane may include expanded polytetrafluoroethylene. The frame may include a plurality of wires. The plurality of wires may include nitinol. The frame may include a cylindrical region that extends a first distance from the occlusive face in a generally distal direction, and the tapered region may extend from a distal end of the cylindrical region to the distal end of the frame. The occlusive device may also include one or more anchors disposed near a junction of the cylindrical region and the tapered region. The frame element may include a petal shape and an apex of the petal shape, and wherein the apex of the petal shape includes a bend in the frame element. The at least one anchor may be located at the apex of the petal shape. The at least one anchor may include a first cuff and a second cuff, where the frame element passes through each of the first and second cuffs, and where the first cuff is positioned on a first side or the apex and the second cuff is positioned of a second side of the apex that is different from the first side.

In a second general aspect, a method of occluding a vessel includes providing an occlusive device that comprises (a) a frame element having a distal end and a proximal end, and a delivery configuration and a deployed configuration; (b) an occlusive face having a peripheral edge, and positioned toward the proximal end of the frame element; and (c) at least one anchor positioned at the peripheral edge of the occlusive face, wherein at least a portion of the at least one anchor extends at an acute angle to the peripheral edge of the occlusive face. The method also includes configuring the occlusive device in the delivery configuration and advancing the occlusive device to a delivery site, and deploying the occlusive device at the delivery site.

In various implementations, the delivery site may be a left atrial appendage. The at least on anchor may engage tissue near an ostium of the left atrial appendage.

Other advantages, benefits, and novel features of the embodiments of the present disclosure will become apparent from the following detailed description and accompanying drawings. All references, publications, and patents, including the figures and drawings included therewith, are herein incorporated by reference in their entirety.

BRIEF DESCRIPTION OF THE DRAWINGS

FIG. 3 is a perspective view of an example frame of the occlusive device of FIG. 1.

FIGS. 10A and 10B are perspective views of the frame of FIG. 3 as engaged with a center pin and prior to being expanded longitudinally.

Like reference numbers and designations in the various drawings indicate like elements.

DETAILED DESCRIPTION

The devices and techniques discussed herein relate to occlusive devices that can be used to occlude holes, defects, or appendages in the body of a patient, including the heart, and methods of making and using the devices. Some implementations of the devices can be used to occlude, without limitation, right or left atrial appendages, fistulas, aneurysms, and patent ductus arteriousus. In some embodiments, the occlusive devices provide a frame that is adequately or sufficiently compliant to conform to a wide variety of opening geometries and sizes. Implementations of devices described herein can be easily loaded into a catheter or sheath, both at a time of initial deployment and at a later time, such as to reposition or remove the device from a deployed location within the body.

Although atrial fibrillation can result in blood clots originating in the left atrial appendage (LAA) and the occlusive devices illustrated herein will be described with regard to the LAA, the occlusive devices described herein can also be used in other areas of the body. Some embodiments of the devices may be used, for example, in a right atrial appendage. In general, implementations of the devices may be used for placement across any appropriate aperture of the body, including apertures in the vasculature where there is a need to prevent blood clots from escaping or to inhibit or substantially reduce blood flow.

Particularly, some embodiments of the occlusive devices can be configured to occlude a LAA. Implementations of devices described herein can be used to conform to the anatomy of a variety of left atrial appendage ostia and can efficiently occlude the LAA, can demonstrate firm and secure anchoring with reduced risk of trauma and bleeding from anchoring, and can provide rapid cessation of blood flow across an occluding membrane included with the devices. The occlusive devices can include a frame that provides firm, secure anchoring to tissue of the LAA with significantly reduced clinical sequela from piercing, or without traumatic piercing, of the LAA tissue. As will be described in more detail below, different types of anchor features may be used with the devices disclosed herein, and the anchor features may be located at or associated with different areas of the devices.

Embodiments of the occlusive devices can include a membrane configured to substantially or completely inhibit passage of blood through the membrane. In some embodiments, the occlusive devices can include a membrane that is configured to induce rapid tissue ingrowth and immediately occlude passage of blood through the membrane.

In some embodiments, the occlusive devices include an occlusive face that is at least partially covered by the membrane and one or more anchors positioned on a peripheral edge of the occlusive face. In some embodiments, one or more anchors may be positioned on portions of the occlusive device that are not on the peripheral edge of the occlusive face.

Figure 1:
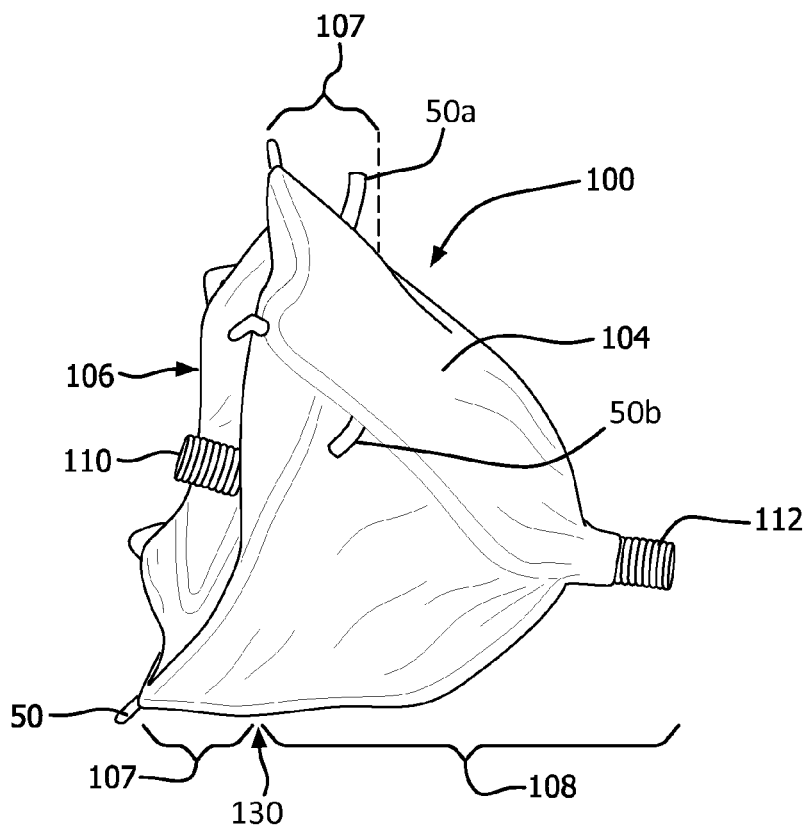
FIG. 1 is side view of an example occlusive device that can be used to occlude a hole, defect, or appendage within a patient.
Figure 2:
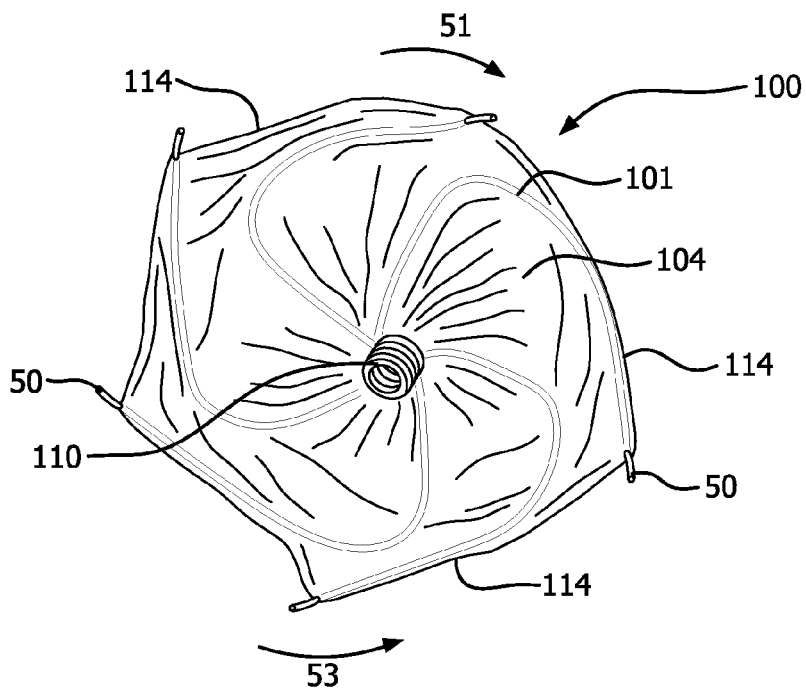
FIG. 2 is a front view of a proximal end of the occlusive device of FIG. 1.

FIGS. 1 and 2 illustrate an embodiment of an example occlusive device 100 that can be used to occlude a structure or a conduit, such as an LAA, within a patient. The occlusive device 100 includes a proximal eyelet 110, a distal eyelet 112, an occlusive face 106, a generally cylindrical region 107 extending from the occlusive face 106 in a distal direction, a tapered region 108 extending from the cylindrical region 107 toward the distal end of the device, and a membrane 104 covering a frame 102 (see FIG. 3) of the occlusive device 100. A lumen can extend through both eyelets 110 and 112 and through the length of device 100.

The occlusive face 106 is configured to conform, while in a deployed configuration, to a shape of an ostium of the LAA, or other biological ostia. For example, the diameter of the occlusive face 106 can be altered or adjusted during deployment of the occlusive device 100 by transmitting torque to the frame 102 via the delivery system. In the example illustrations of FIGS. 1 and 2, the occlusive face 106 has a concave shape. However, in other examples, the occlusive face 106 can have a convex shape or a flat or planar shape. An adaptability of the occlusive face 106 can allow versatility in sizing of the occlusive device 100 and facilitate placement of the occlusive device 100 in an ostium of an LAA, which are often irregularly shaped and may differ substantially in size from one patient to another.

In a general embodiment, the generally cylindrical region 107, which can extend distally from the occlusive face 106, can be of any appropriate length. Accordingly, the length of the cylindrical region 107 can allow for variances in the ostium of the LAA or LAA shape variances. For example, in some embodiments, the cylindrical region 107 may have a length from about 0.2 cm to about 0.7 cm, and in some embodiments, a length of about 0.5 cm. Similarly, the tapered region 108, which extends from the cylindrical region 107 to the distal eyelet 112, can be of any appropriate length. For example, in some embodiments, the tapered region 108 may have a length from about 0.6 cm to about 1.2 cm, and, in some embodiments, a length of about 1.0 cm. Furthermore, a profile of the tapered region 108 can have any suitable slope with respect to a longitudinal axis of the device to provide sufficiently secure positioning of the occlusive device 100 within an inner region of the LAA. For example, the tapered region 108 can be configured to conform to a variable taper of the inner region of an LAA. A junction 130 may define a boundary between the cylindrical region 107 and the tapered region 108.

In the example of FIGS. 1 and 2, the eyelets 110 and 112 have a substantially cylindrical shape. However, the eyelets 110 and 112 can generally be provided in a variety of shapes, such as a rectangular shape, other polygonal shape, or an irregular shape. One or both of eyelets 110 and 112 can be formed to engage one or more components of a delivery system (e.g., a delivery catheter) that can be used to deliver the occlusive device 100 to a delivery site within a patient. For example, engagement of a delivery catheter with either or both of the eyelets 110 and 112 may allow a torque to be applied to and maintained on the occlusive device 100. In some embodiments, an application of torque to the occlusive device 100 may facilitate placement of the device and, in some embodiments may facilitate engagement of anchors or anchor features of the device with tissue at the delivery site.

The device 100 can include anchors 50, 50a, 50b, 60 (FIG. 4A) attached to portions of the frame 102 of the device. See FIGS. 1, 2, 3, 4A, 4B, 10A, 10B, and 11A for examples of anchors that can be used. Some anchors 50 may be attached to frame portions that form a peripheral edge 114 of the occlusive face 106 of the occlusive device 100, as shown in FIGS. 1 and 2. The occlusive face 106 may be structurally formed from the proximal end of the multi-wire frame 102. As described above, in the depicted example of FIGS. 1 and 2, the occlusive face is concave, and this may facilitate projection of the anchors 50 on the peripheral edge 114 of the occlusive face 106 in a proximal or partially proximal direction, with respect to a longitudinal dimension of the device. As such, in some embodiments the anchors 50 on the peripheral edge 114 of the occlusive face may be non-planar with the peripheral edge 114 of the occlusive face 106 (because they project proximally). Anchors that protrude proximally along an axial orientation of the device may provide advantages for engaging tissue and preventing migration of the device following deployment (e.g., may prevent the device from moving from the appendage).

In other embodiments, the anchors 50 on the peripheral edge 114 of the occlusive face may be planar with the peripheral edge 114 of the occlusive face 106 (that is, located within or substantially within a plane defined by the peripheral edge 114). For example, the anchors may project tangentially from a portion of the wire frame that is proximate to the anchor 50. In yet other embodiments, the anchors may be shaped to project in a distal or partially distal direction from the peripheral edge 114 of the occlusive face 106, and may thus also be considered non-planar with the peripheral edge 114.

Relatedly, for embodiments where the occlusive face has a convex profile or a planar profile, in various implementations the anchors 50 positioned on a peripheral edge of the occlusive face may similarly be oriented to project in a proximal, partially proximal, distal or partially distal direction with respect to a longitudinal dimension of the device, and in such cases may be considered non-planar with the peripheral edge of the occlusive face. Alternatively, the anchors may be located within a same plane as the peripheral edge of the occlusive face. In some implementations, anchors may project tangentially from a portion of the wire frame that is proximate to the anchor 50.

Figure 10A:
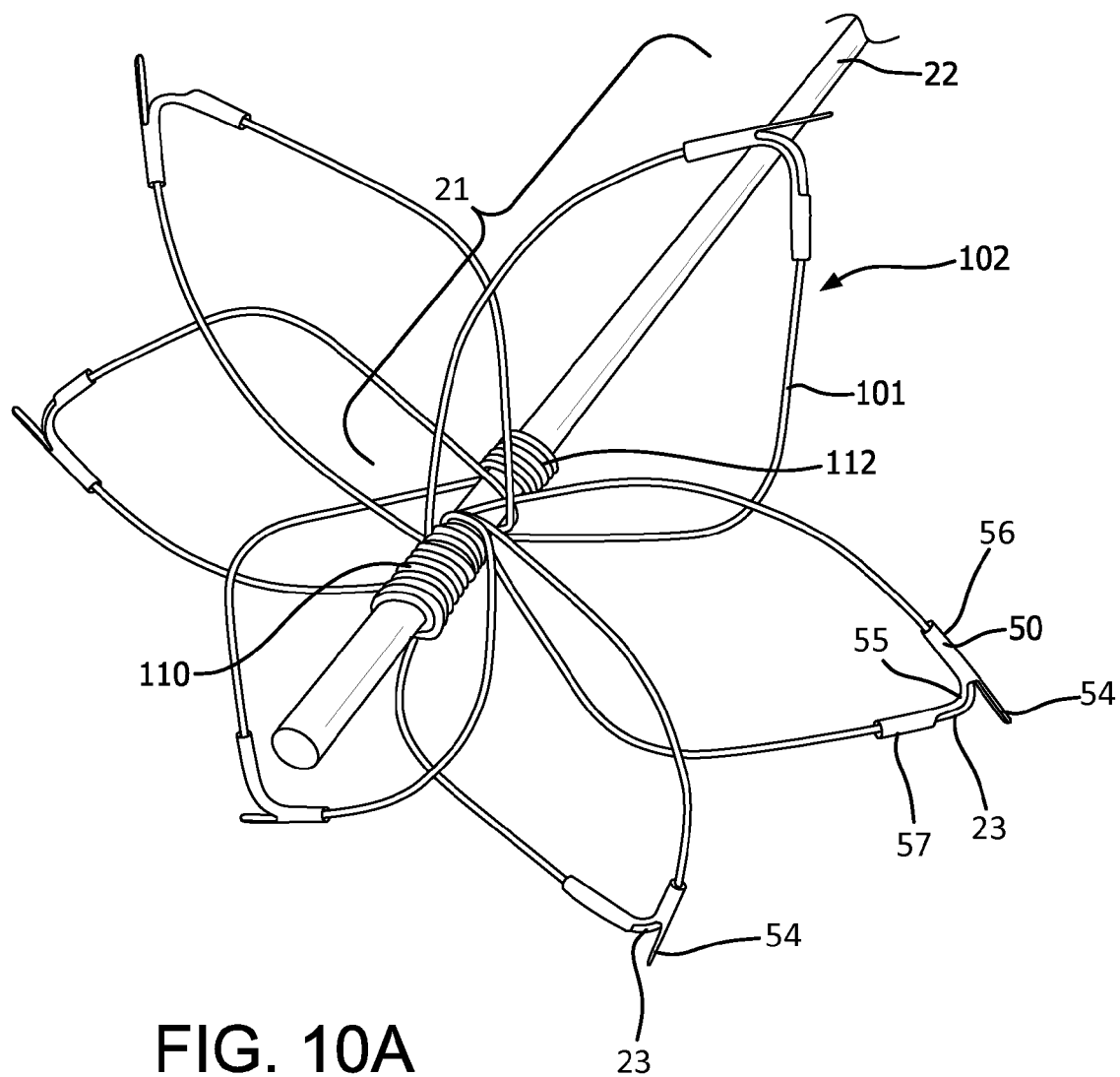

As can be seen with reference to FIG. 10A, the frame may include petals 21 that define the occlusive face 106 of the device 100. The petals 21 of the frame 102 may be fanned in a same direction as the helical winding of the wires 101 around the eyelets 110 and 112, as will be explained in more detail below. In one example, each petal 21 is offset by about 60 degrees relative to the adjacent petal 21. Petal shape may be varied (e.g., by changing a radius from eyelet to petal apex), and more or fewer petals 21 can be used. For implementations that use different numbers of wires 101 and petals 21, the petals 21 may be offset by other amounts. For example, for a four-wire device with four petals, each petal may be offset by about 90 degrees relative to the adjacent petal. For a five-wire device with five petals, each petal may be offset by about 72 degrees relative to the adjacent petal. For an eight-wire device with eight petals, each petal may be offset by about 45 degrees relative to the adjacent petal. As can be seen with reference to FIG. 10A, each petal 21 may overlap a portion of an adjacent petal 21. Petal width may change as more or fewer petals are included, for example. The petals include apices 23. Petal width may be tuned to provide desirable apposition features depending on application. For example, as petal width is increased, such that a larger radius from eyelet 110 to petal apex 23 is provided, less apposition force may be imparted from the device to surrounding tissue at the apex 23 of the petal 21, and conversely as petal width is decreased, such that a smaller radius from eyelet 110 to petal apex 23 is provided, more apposition force may be imparted from the device to surrounding tissue at the apex 23 of the petal 21. In this manner, the tissue apposition characteristics of the device may be tuned based on device winding parameters.

As can be seen with reference to FIG. 10A, anchors 50 may be located at or near apices 23 of the petals 21 of the device. A first cuff 56 may be located on a first side of the apex 23 and a second cuff 57 may be located on a second side of the apex 23. When the device is in an elongated delivery configuration, such as when constrained within a lumen of a delivery catheter or sheath as the device is delivered, the eyelets 110, 112 are separated such that the elongate members 101 are pulled substantially straight or linear in the delivery configuration. In the delivery configuration, anchors 50 are similarly pulled substantially straight or linear, such that a tissue engagement portion 54 of the anchors 50 may be substantially in contact with the corresponding elongate member 101. For example, the elongate member 101 may tuck into an area proximate the tissue engagement portion 54.

As the device is deployed from the catheter and enters the less restrictive environment of the body cavity at the delivery site, the device assumes its deployed configuration (e.g., based on shape memory properties of the elongate members 101). Accordingly, the elongate members 101 form bends with apices 23 in the deployed configuration, and the elongate members 101 cause the anchor joining portion 55 that connects a first cuff 56 with a second cuff 57 of the anchor to bend and conform with the elongate member 101. The cuff joining portion 55 may bend in this way because it may be more flexible than the elongate member 101, in some implementations. When this occurs, the tissue engagement portion 54 of the anchor may remain generally straight, so that as the apices 23 develop the tissue engagement portion 54 effectively creates a high contact force against tissue at the delivery site. In examples for occluding the LAA, the deployment of the device may create a high contact force in the area near the ostium of the appendage. In some examples, anchors are not included with the device, and the apices 23 of the elongate members may create a high-contact force on deployment of the device, and in such cases the elongate members themselves may anchor the device in position. Similarly, in some examples the anchors 50 may include tissue engagement portions 54 designed to atraumatically engage tissue without penetrating the tissue.

In some examples, one or more anchors 50 may be disposed on the frame 102 in the cylindrical region 107 on the frame 102, for example, just proximal to the junction 130 (see, e.g., anchor 50*a* in FIG. 1). In some examples, one or more anchors 50 may be disposed on the frame 102 in the tapered region 108 on the frame 102, for example, just distal to the junction 130 (see, e.g., anchor 50*b* in FIG. 1). In some examples, anchors 50 may be disposed on the frame 102 in the cylindrical region 107 and in the tapered region 108. In such examples, the anchors may be disposed on bends 115 having relatively large bend radii or along a portion of the frame 102 that is substantially straight. In a general embodiment, the occlusive device 100 can include any appropriate number of anchors 50. In some implementations, anchors 50*a* and 50*b* may be omitted.

The anchors 50 may extend from the frame 102 (e.g., from the frame 102 in the cylindrical region 107, in the tapered region 108, at the junction 130, or along the peripheral edge 114 of the occlusive face 106), or combinations and sub-combinations thereof, at various angles with respect to a portion of the frame proximate the anchor (e.g., at an acute angle, at a right angle, or at an obtuse angle). In some examples, one or more of the anchors 50 may extend tangentially from a portion of the frame 102 near the anchor (e.g., from the frame 102 in the cylindrical region 107, in the tapered region 108, at the junction 130, or along the peripheral edge 114 of the occlusive face 106). In some examples, one or more, or all, of the anchors 50 may extend from the frame 102 in a generally clockwise direction, as indicated by the arrow 51 in FIG. 2. In some examples, one or more, or all, of the anchors 50 may extend from the frame 102 in a generally counterclockwise direction, as indicated by the arrow 53 in FIG. 2. In some examples, an occlusive device 100 may include some anchors 50 that extend from the frame 102 in a generally clockwise direction and some anchors 50 that extend from the frame 102 in a generally counterclockwise direction. The anchors 50 can be made of any suitable material, such as a non-permanent biodegradable or bioabsorbable material. For example, the anchors 50 can be made of NiTi, L605 steel, stainless steel, or any other appropriate biocompatible material. In some examples, anchors may be made of different materials (e.g., not all anchors made of same material).

An embodiment can have anchors protrude or project tangentially to the peripheral edge 114 of the occlusive face 106. An embodiment can have anchors protrude or project substantially tangentially to the peripheral edge 114 of the occlusive face 106. An embodiment can have anchors protrude or project at an acute angle to the peripheral edge 114 of the occlusive face 106 in the same or substantially the same plane as the occlusive face 106. In some examples, the tissue engagement portion of the anchor may protrude at an acute angle of about 30-60 degrees, and in some cases at about 20 degrees, or about 30 degrees, or about 40 degrees, or about 50 degrees, or about 60 degrees. In some implementations, an anchor that protrudes at an acute angle to the peripheral edge 114 and in the same plane with respect to the occlusive face 106 may provide advantages for deliverability of the device and for recapturability of the device into the delivery catheter, for example if it is desired to remove or reposition the device.

For additional information regarding types of anchors that can be used with the devices disclosed herein, see co-pending U.S. patent application titled, "Medical Device Fixation Anchors," filed 13 Sep. 2012, with Edward E. Shaw as inventor, the entire contents of which are hereby incorporated by reference for all purposes.

The occlusive device 100 can be made from a multi-elongate-member frame 102. In some implementations, the elongate members can be wires, and hereafter may be referred to as wires for simplicity. Multi-wire frame 102 can be made from multiple individual lengths of relatively flexible, fatigue resistant elongate members 101, e.g., wires. The multi-wire frame 102 can be semi-rigid. Expandable frame 102 can be constructed from any number of fatigue resistant elongate members 101. The expandable frame 102 can be formed in any size appropriate for an application. The size of a human left atrial appendage ostium ranges from about 10 to about 32 mm with the average being about 21 mm plus or minus about 4 mm. Device sizes can be manufactured to encompass the entire range of ostium sizes. An embodiment can have multiple elongate members, e.g. four, five, six, seven, eight, nine, or more wires used in the manufacture of the device. The expandable frame 102 can be constructed from wires, for example fatigue resistant wires, that have elastic properties. The expandable frame 102 can be constructed of wires that have elastic properties that allow for expandable frame 102 to be collapsed for catheter-based delivery or thoracoscopic delivery, and to self-expand to the desired configuration once positioned in a cavity. The elastic wire can be a spring wire, a shape memory alloy wire or a super-elastic alloy wire. Any wire can be used that has biocompatible characteristics and is strong, flexible, and resilient. For example, the wire can be nitinol, L605 steel, stainless steel, or any other biocompatible wire. The elastic wire can also be of a drawn-filled type of nitinol containing a different metal at the core. The super-elastic properties of nitinol make it a useful material for this application. Nitinol wire can be heat set into a desired shape. Stainless steel wire is an alternative material. It can be plastically deformed into a desired shape. Wire that is formed with a centerless grind technique to have multiple diameters can also be used. Other shape memory or plastically deformable materials can also be suitable in this application. In one embodiment, expandable frame 102 can be constructed of a drawn-filled type of NiTi wire containing a radiopaque metal such as platinum at the center. Upon deployment, the wire structure resumes its deployed shape without permanent deformation. Expandable frame 102 and other embodiments of the expandable frames can be formed from elastic wire materials that have outer diameters (OD) between about 0.12 and about 0.4 mm. Other embodiments can be formed from wires with an OD of about 0.3 mm.

The multi-wire frame 102 can be partially or substantially covered with membrane 104. As shown in FIGS. 1 and 2, a membrane component 104 is configured to inhibit passage of blood. Embodiments can provide a membrane component 104 configured to inhibit the passage of blood through the membrane, i.e., substantially occludes the flow of blood through the membrane. Other embodiments can provide a membrane component 104 that is configured to induce rapid tissue ingrowth that and immediately occludes the passage of blood through the membrane. In an embodiment, the membrane component 104 provides for a blood or body fluid impermeable membrane that occludes the flow of blood or bodily fluids through the membrane yet promotes the ingrowth and endothelialization. Such an embodiment can comprise a fluoropolymer membrane such as an expanded polytetrafluoroethylene polymer membrane. The inhibition of blood or bodily fluid passage across the membrane component 104 may be immediate and may not rely on the thrombotic process. Membrane component 104 can also serve as a tissue ingrowth scaffold for durable occlusion and anchoring of the device.

The microporous structure of the membrane component 104 can be tailored to promote tissue ingrowth and/or endothelialization. The membrane component 104 can be modified by various chemical or physical processes to enhance certain mechanical or physical properties. A hydrophilic coating can be applied to membrane component 104 to promote its wetability and echo translucency. Additionally, a physiochemical modification can be employed whereby the membrane component 104 includes chemical moieties that promote endothelial cell attachment, migration, and/or proliferation or resist thrombosis. A surface modified with covalently attached heparin is one example of a membrane modification. The membrane component 104 can be permanently implanted across the ostium. The membrane component 104 can be made of any biocompatible materials, including fluoropolymers such as polytetrafluoroethylene and expanded polytetrafluoroethylene; polyesters; silicones; urethanes; or other biocompatible polymers and combinations thereof. An embodiment can comprise a membrane component comprising a fluoropolymer such as polytetrafluoroethylene or expanded polytetrafluoroethylene. In another embodiment, the membrane component comprises expanded polytetrafluoroethylene.

Referring now to FIG. 3, the occlusive device 100 includes a frame 102 formed of multiple elongate members or wires 101. While the frame 102 is shown as including six wires 101 in the embodiment of FIG. 3, a frame 102 can generally include any appropriate number of wires 101 (e.g., four, five, seven, eight, nine, ten, or more wires 101). The wires 101 form, and extend from, proximal eyelet 110 at a proximal end of the frame 102 to distal eyelet 112 at a distal end of the frame 102, where distal eyelet 112 is formed by the wires 101. Between the eyelets 110 and 112, the wires 101 fan out to provide occlusive features and anchoring features for the device 100. The occlusive face 106, for example, is provided near the proximal end of the frame 102. As shown in FIG. 3, the frame 102 of the device 100, and in particular the proximal eyelet 110 and the distal eyelet 112, are shown mounted on a mandrel 44, which can be used in making the device 100, as will be described below. A spacer tube 52 extends between the proximal eyelet 110 and the distal eyelet 112 and over mandrel 44 to separate the eyelets 110, 112 by a desired amount.

Figure 4A:
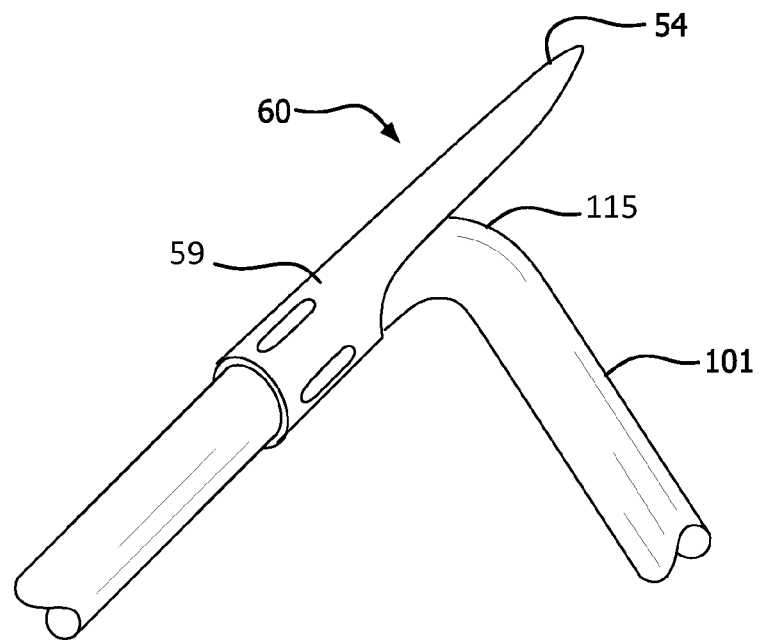
FIGS. 4A and 4B are enlarged perspective views of a portion of the frame of FIG. 3.
Figure 4B:
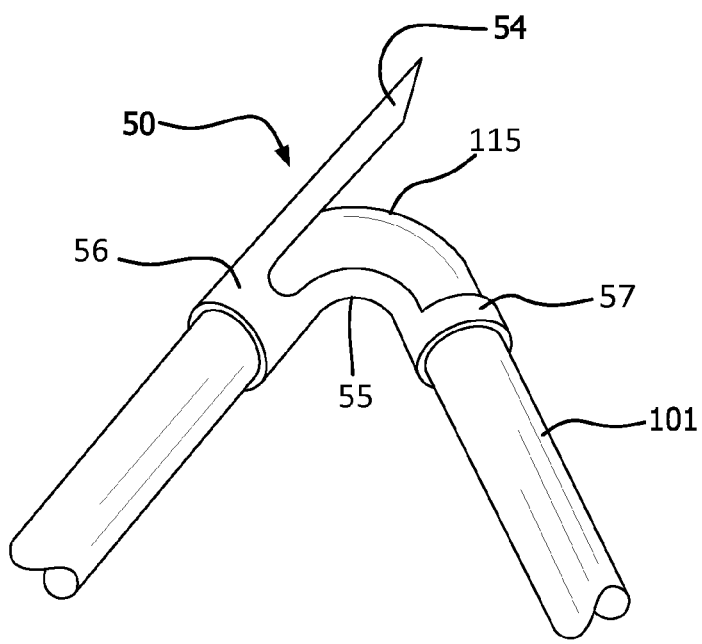

Embodiments of anchors 50 and 60 are shown in FIGS. 4A-B. FIG. 4A depicts an anchor 60 cut from a length of nitinol tube and having a tissue engagement member 54 (e.g., a barb) and an anchor retaining cuff 59. Anchor retaining cuff 59 can be attached to wire 101 by any suitable method. Anchor retaining cuff can be attached to wire 101 by means of mechanical fit, welding or adhesive. FIG. 4B depicts an anchor 50 with tissue engagement member 54, first anchor retaining cuff 56, and second anchor retaining cuff 57. Anchor (50, 60) can be sized to have an inner diameter that would accommodate any of the wire 101 sizes needed to form a device 100. Any one or both of anchor 50 and 60 can be used alone or in combination. Elongate member bends 115 may correspond to apices 23 in FIG. 10A, for example.

In some examples, the bends 115 can provide, for example, anchoring features to the frame 102 even if anchors 50, 60 are not used. For example, the bends 115 may be adapted to contact, engage, or puncture a tissue at a delivery site (e.g., the LAA) in order to anchor the occlusive device 100 to the delivery site, and in such examples the wire bends 115 themselves may be considered primary anchors or to provide primary anchoring features. In this manner, one or more portions of the frame 102 of the device 100 may be used to anchor the device at a delivery site.

Referring again to FIG. 3, the wires 101 can be relatively flexible, fatigue-resistant, and semi-rigid, such that the frame 102 can take on a prescribed shape in a deployed configuration and can collapse to a delivery configuration upon insertion into a component of a delivery system (e.g., a delivery sheath). The wires 101 can be, for example, fatigue resistant wires that have elastic properties. The elastic properties can allow the frame 102 to collapse for catheter-based delivery or thoracoscopic delivery and to self-expand to a desired configuration when positioned in a cavity. The wires 101 can be spring wires, shape memory alloy wires, or super-elastic alloy wires. In some examples, one or more portions of the wires 101 may be more or less flexible than one or more other portions of the wires 101. In general, the wires 101 can include any elongate member that has biocompatible characteristics and is sufficiently strong, flexible, and resilient.

The wires 101 can be made of nitinol (NiTi), L605 steel, stainless steel, or any other appropriate biocompatible material. The wires 101 can also be made of a drawn-filled type of NiTi and include a metal core made of a different material. Super-elastic properties of nitinol make NiTi a particularly good candidate material for such wires 101 (e.g., NiTi wires can be heat set into a desired shape). In some embodiments, wires 101 made of stainless steel can be plastically deformed into a desired shape. In some embodiments, the wires 101 may be formed with a centerless grind technique to have variable diameters. In some embodiments, the wires 101 may be made of other shape memory or plastically deformable materials. In some embodiments, the wires 101 may be made of a drawn-filled type of NiTi wire that includes a radiopaque metal, such as platinum, at centers of the wires 101. Upon deployment, such wires 101 can resume their deployed shape without being permanently deformed. In some embodiments, the wires 101 may have an outer diameter of about 0.12 mm to about 0.4 mm (e.g., 0.3 mm). The wires 101 may have any appropriate cross-sectional shape. For example, in some embodiments the wires 101 may have a round, oval, square, rectangular, diamond, or other polygonal cross-sectional shape. In some implementations, the wires 101 may include a textured surface that may provide greater resistance to dislodgement when contacting tissue at a delivery site, whether in direct contact with the tissue or in contact via the membrane 104, which may be disposed between the wire 101 and the tissue.

Referring again to FIGS. 1 and 2, the frame 102 can be partially or substantially covered with the membrane 104, which is configured to inhibit passage of blood (i.e., the membrane 104 can substantially occlude the flow of blood through the membrane 104). In some embodiments, the membrane 104 is configured to induce rapid tissue ingrowth and can immediately occlude the passage of blood through the membrane 104. In some embodiments, the membrane 104 is impermeable to blood or other bodily fluids. In some examples, the inhibition of blood or bodily fluid passage across the membrane 104 is immediate and does not rely on a thrombotic process. In some embodiments, the membrane 104 can have a microporous structure that provides a tissue ingrowth scaffold for durable occlusion and anchoring of the occlusive device 100. In some embodiments, the membrane 104 can provide a microporous structure that promotes endothelialization. Some such embodiments of the membrane comprise a fluoropolymer such as an expanded polytetrafluoroethylene (ePTFE) polymer.

In some examples, the membrane 104 can be modified by various chemical or physical processes to enhance certain mechanical or physical properties. For example, a hydrophilic coating can be applied to the membrane 104 to provide or improve wetability and echo-translucency of the membrane 104. In some embodiments, the membrane 104 can be modified with chemical moieties that promote one or more processes including endothelial cell attachment, cell migration, cell proliferation, and resistance to thrombosis. For example, the membrane 104 can be modified with covalently attached heparin. In some examples, the membrane 104 may be configured to be permanently implanted across the ostium of the LAA. The membrane 104 can be made of any suitable biocompatible material, including fluoropolymers, such as polytetrafluoroethylene (PTFE) and ePTFE; polyesters; silicones; urethanes; or other biocompatible polymers and combinations thereof.

Still referring to FIGS. 1 and 2, the occlusive device 100 can, and as describe above, in some embodiments, include one or more anchors 50 disposed on one or more regions of the frame 102, where the anchors 50 can be adapted to puncture a tissue at the delivery site in order to anchor the occlusive device 100 at the delivery site. In some examples, the anchors may be configured to atraumatically contact tissue without piercing the tissue. The membrane 104 can include holes that allow the anchors 50 to pass through the membrane 104, or the anchors can simply puncture through the membrane 104 in some implementations.

In some examples, one or more anchors 50 can be disposed on one or more of the bends or apices 115 (see FIGS. 3, 4A, 4B) along a peripheral portion of the frame 102 and extend through the membrane 104 at a peripheral edge 114 (see FIGS. 1, 2) of the occlusive face 106. In some examples, the anchors 50 may be disposed on bends 115 that have larger or smaller radii than the bends 115 depicted in FIGS. 4A and 4B. In some embodiments, one or more anchors 50 may be disposed on a region of the frame 102 that is spaced apart from the peripheral edge 114 of the occlusive face 106. For example, one or more anchors 50 may be disposed on a bend 115 (e.g., a bend 115 that has a relatively large radius) of the frame 102 near a junction 130 where the occlusive device 100 transitions from the cylindrical region 107 to the tapered region 108.

With reference to FIGS. 5-8C, an example of assembling an occlusive device, such as device 100, will be described. A 10% platinum drawn filled NiTi wire (e.g., from Fort Wayne Metals, Fort Wayne, Ind.) with a diameter of about 0.23 mm and a length of about 1 m is obtained to form the wires 101 of the occlusive device 100. Specific lengths of the wires 101 may or may not be measured, but the wires 101 should be long enough to complete a winding pattern as described in the following paragraph. In some examples, the wires 101 are obtained having been electropolished. Electropolishing NiTi imparts certain well known properties. For example, electropolishing can induce spontaneous formation of a titanium dioxide layer on a surface of the wires 101, selectively reducing the amount of nickel on the surface of the wires 101, reducing some stresses in the wires 101, and thus improving fatigue properties of the wires 101.

Figure 5:
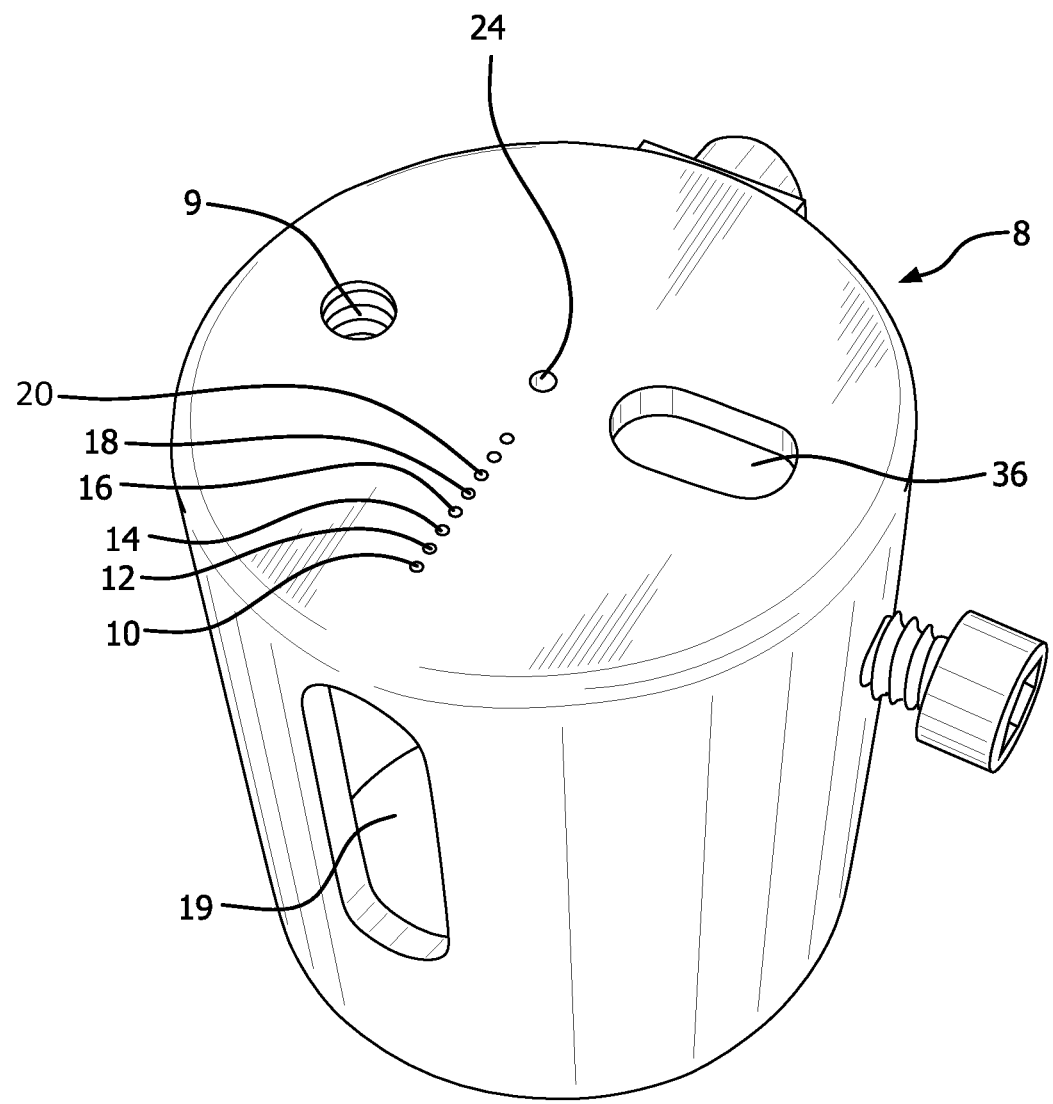
FIG. 5 is a perspective view of an example jig that can be used to make the occlusive device of FIG. 1.
Figure 6:
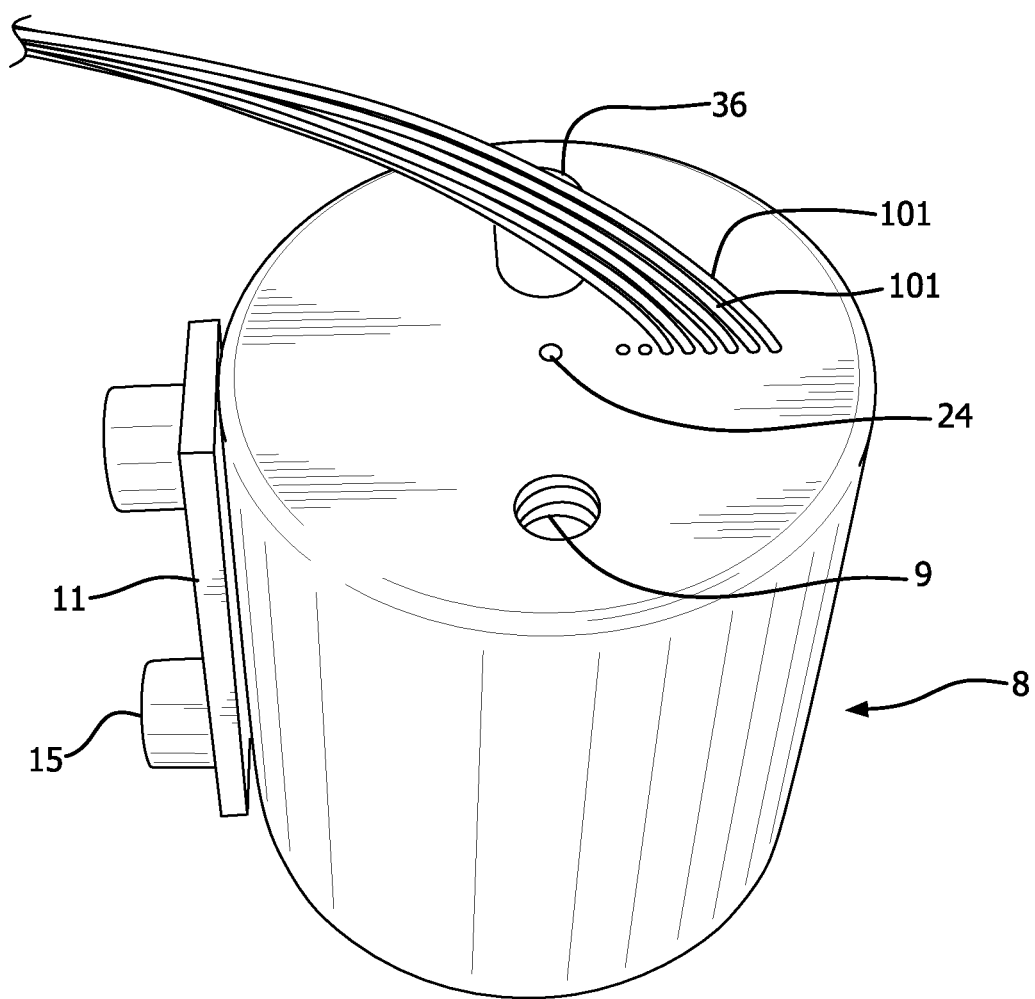
FIG. 6 is a perspective view of the jig of FIG. 5 with wires of the frame of FIG. 3.
Figure 7:
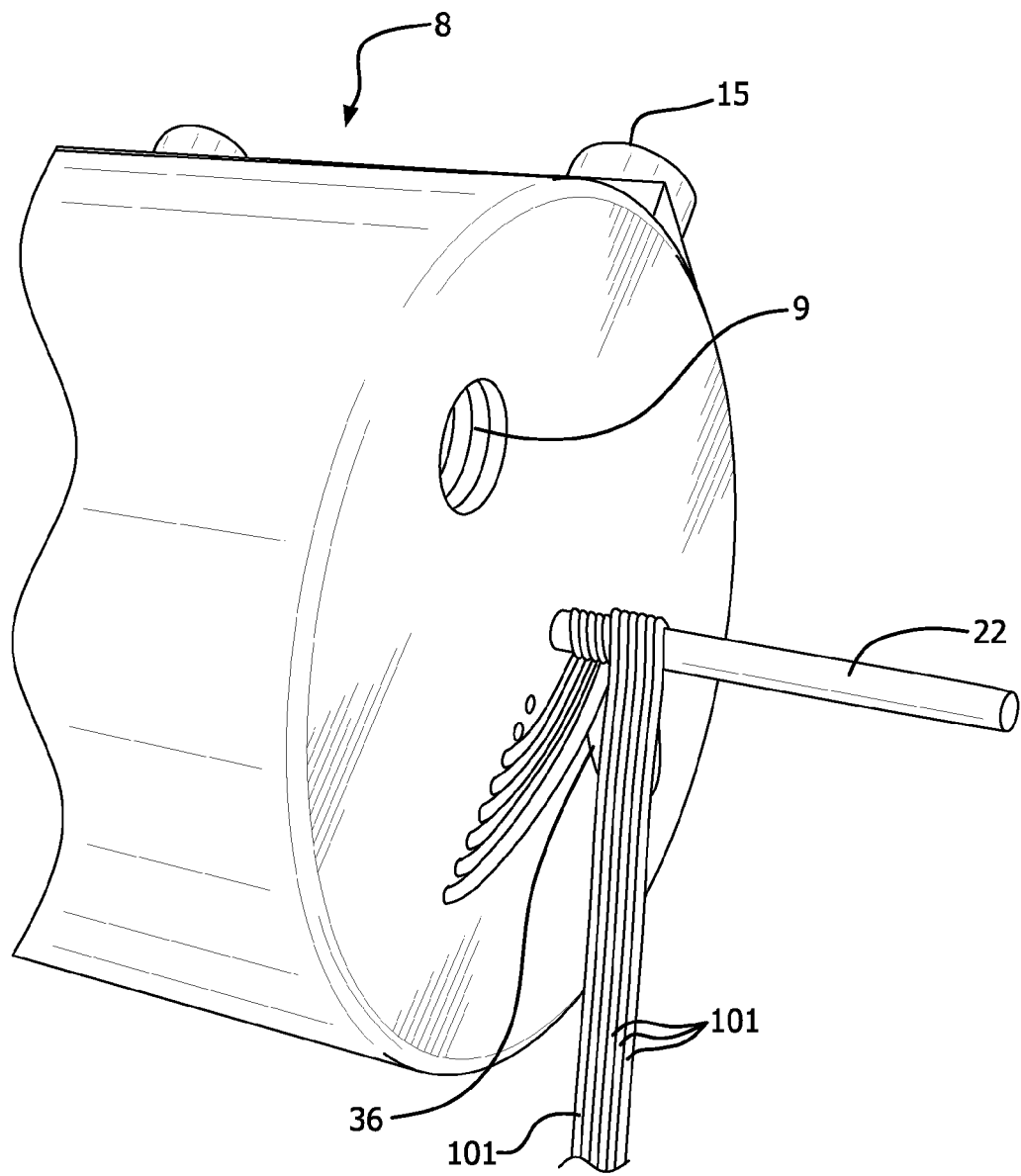
FIG. 7 is a perspective view of the jig of FIG. 5 with the wires of FIG. 6 shown in a winding pattern.

FIG. 5 shows a base jig 8 that can be used to wind an occlusive device, such as device 100. Three wires 101, each having a length of about 1 meter, are folded in half, and free ends of the wires 101 are fed through wire feed holes 10, 12, 14, 16, 18, and 20. For example, the wires 101 are passed through a funnel-shaped opening 19 and then exit the small feed holes 10, 12, 14, 16, 18 and 20 at a bottom of the opening 19. Referring particularly to FIG. 6, the wires 101 exit through the holes 10, 12, 14, 16, 18 and 20 at a flat end surface of the base jig 8. Weights are attached to the free ends of the six wires 101 to hold the wires 101 taut and in place. Referring particularly to FIGS. 5 and 7, the base jig 8 is secured in a chuck of a lathe, and a center pin 22 is inserted into a center pin hole 24 (see FIG. 5) in the base jig 8, deep enough to securely seat the center pin 22 (see FIG. 7). The base jig 8 is positioned so that the wire feed holes 10, 12, 14, 16, 18 and 20 are oriented vertically above the center pin 22, and the wires 101 are positioned on a trailing side of the center pin 22.

Figure 8A:
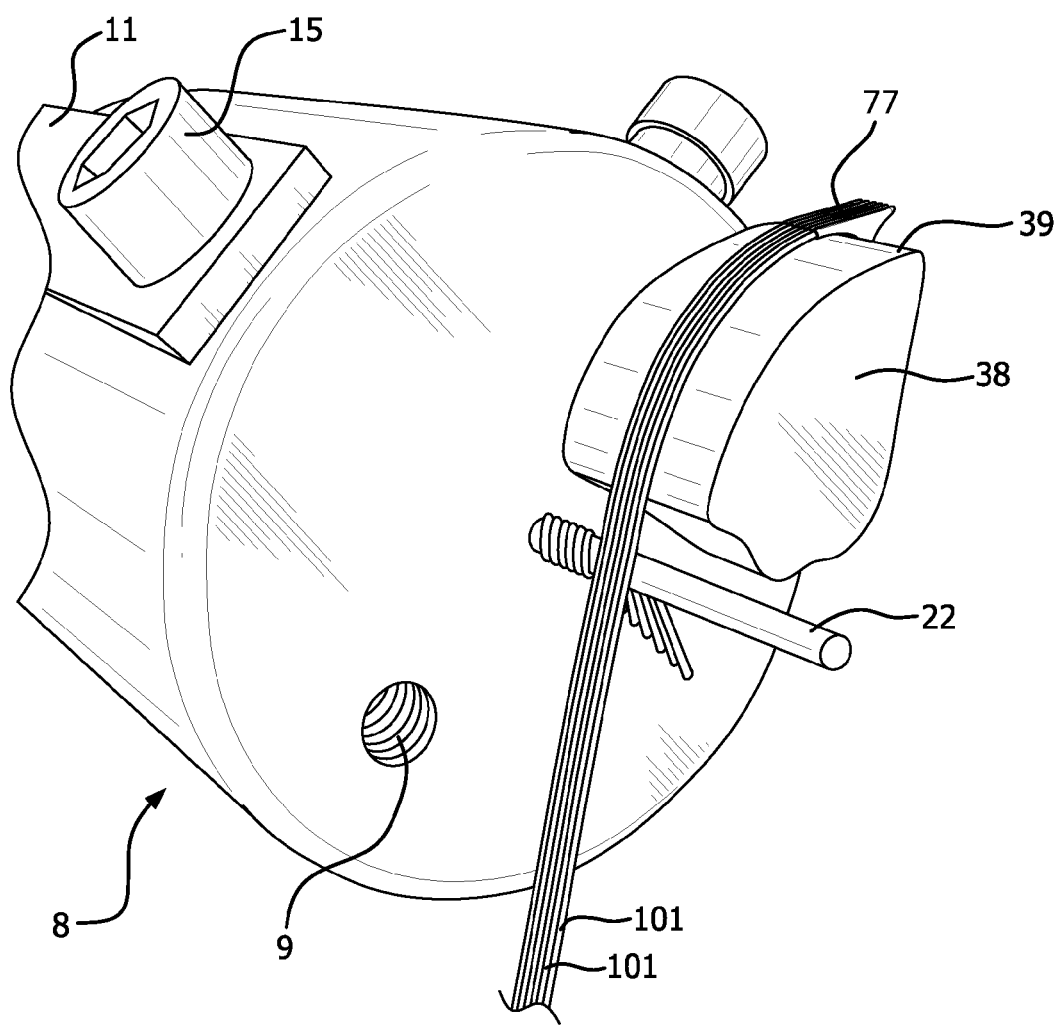
FIGS. 8A, 8B, and 8C are perspective views of the jig of FIG. 5 with the wires of FIG. 6 wound to form portions of the frame of FIG. 3.
Figure 8B:
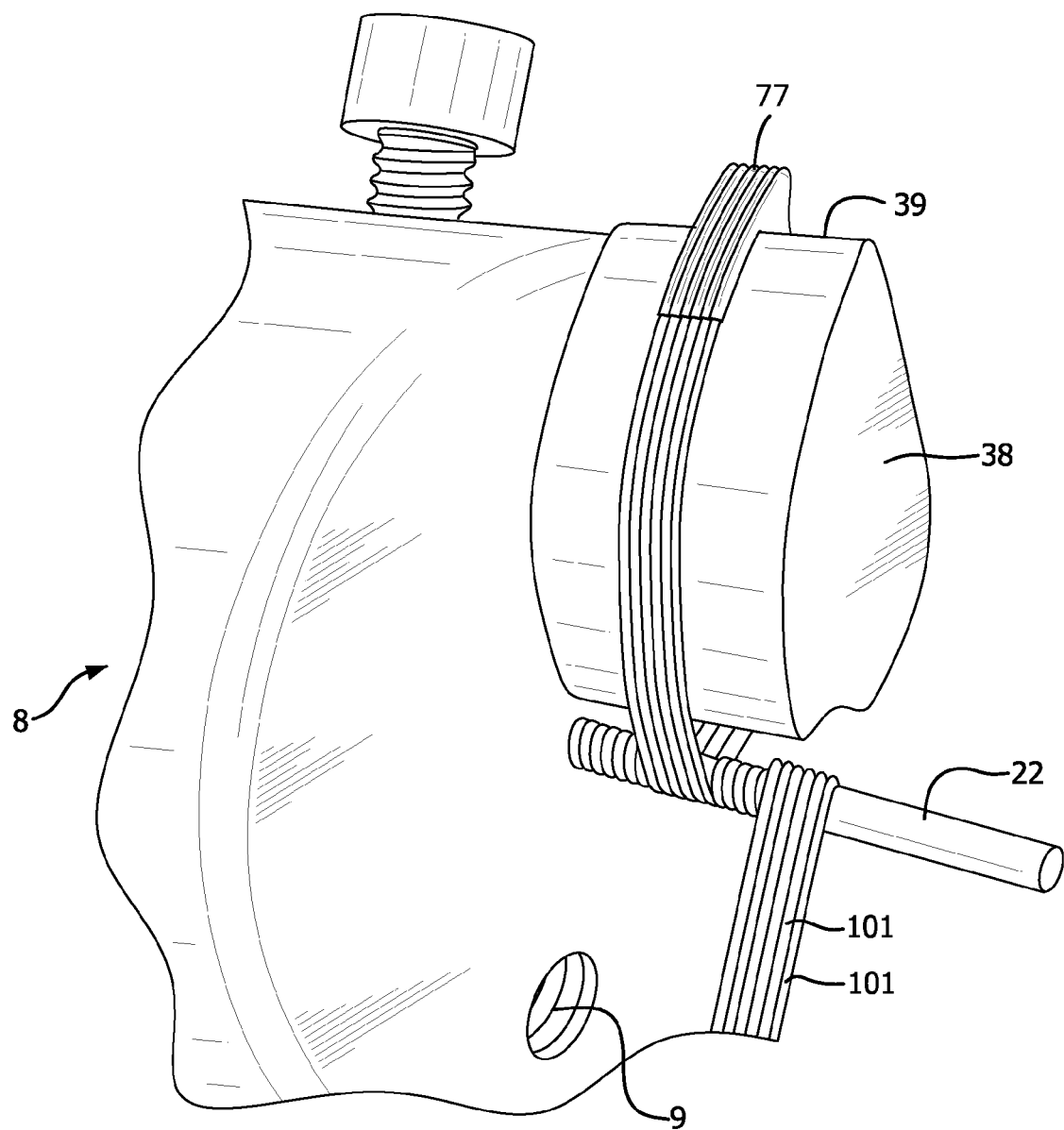
Figure 8C:
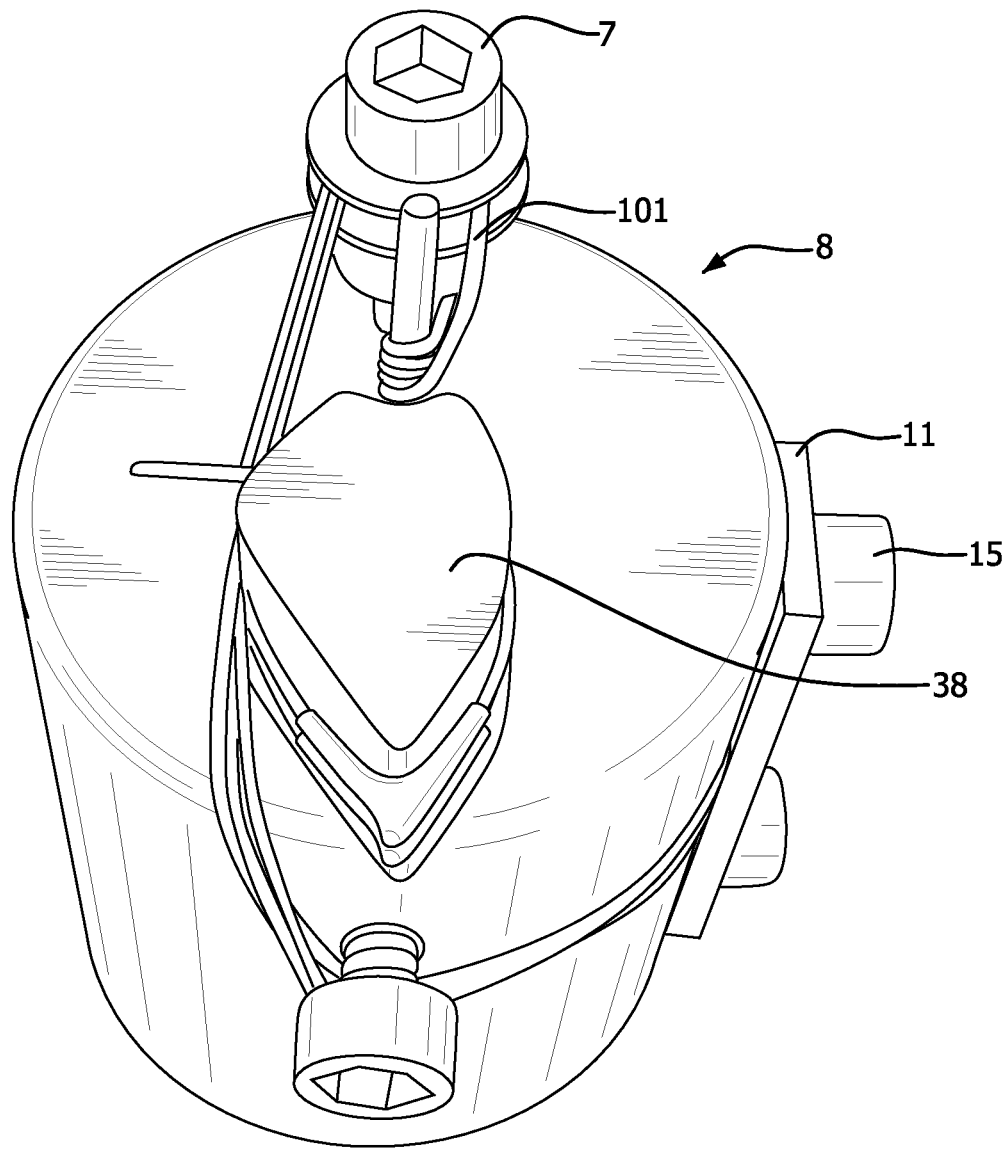

Referring particularly to FIG. 7, a petal jig hole 36 is rotated about 720 degrees to create the proximal eyelet 110 of the occlusive device 100 by causing the wires 101 to wind around the center pin 22. Referring particularly to FIG. 8A, a petal jig 38 is inserted into the petal jig hole 36. Without crossing the wires 101, the wires 101 are placed on top of the petal jig 38. In some examples, anchors, such as the anchors 50 shown in FIGS. 1 and 2, can be attached to the wires 101. For example, one or more anchors 50 may be attached (not shown) to one or more wires 101 at or near an apex of the wires when the device 100 is in a deployed position, and the apex may correspond to a location where the wires wrap around a rounded edge 39 of the petal jig 38. In this manner, the anchors may be located at or near the peripheral edge 114 (see FIG. 1) of the occluding face 106 of the device 100 when in a deployed position. In other examples, one or more anchors 50 may be attached to one or more wires away from an apex or the location where the wires wrap around a rounded edge 39 of the petal jig 38. For example, one or more anchors 50 may be attached to one or more wires 101 about 0.1 cm, 0.2 cm, 0.3 cm, or 0.4 cm from the location where the wires wrap around a rounded edge 39 of the petal jig 38, in either direction as appropriate (e.g., along the gently curved portion of the petal jig 38). The anchors may be attached by any of the known attachment methods, such as adhesive, weld, crimp, entrapment, interference, or by making them an integral part of the frame. In some examples, the anchors 50 may include a generally "V" shape and be formed from a tube with an inner diameter sized to accommodate an outer diameter of the wire 101. The anchors 50 may be slipped over the wire and into a position with respect to the petal jig 38, as shown in FIGS. 8A, 8B, and 8C where the "V" shaped anchors are positioned over the wires 101 at the rounded edge 39 of the petal jig 38. In this manner, the anchors may be located at an apex of the device 100 when in a deployed position.

Figure 9:
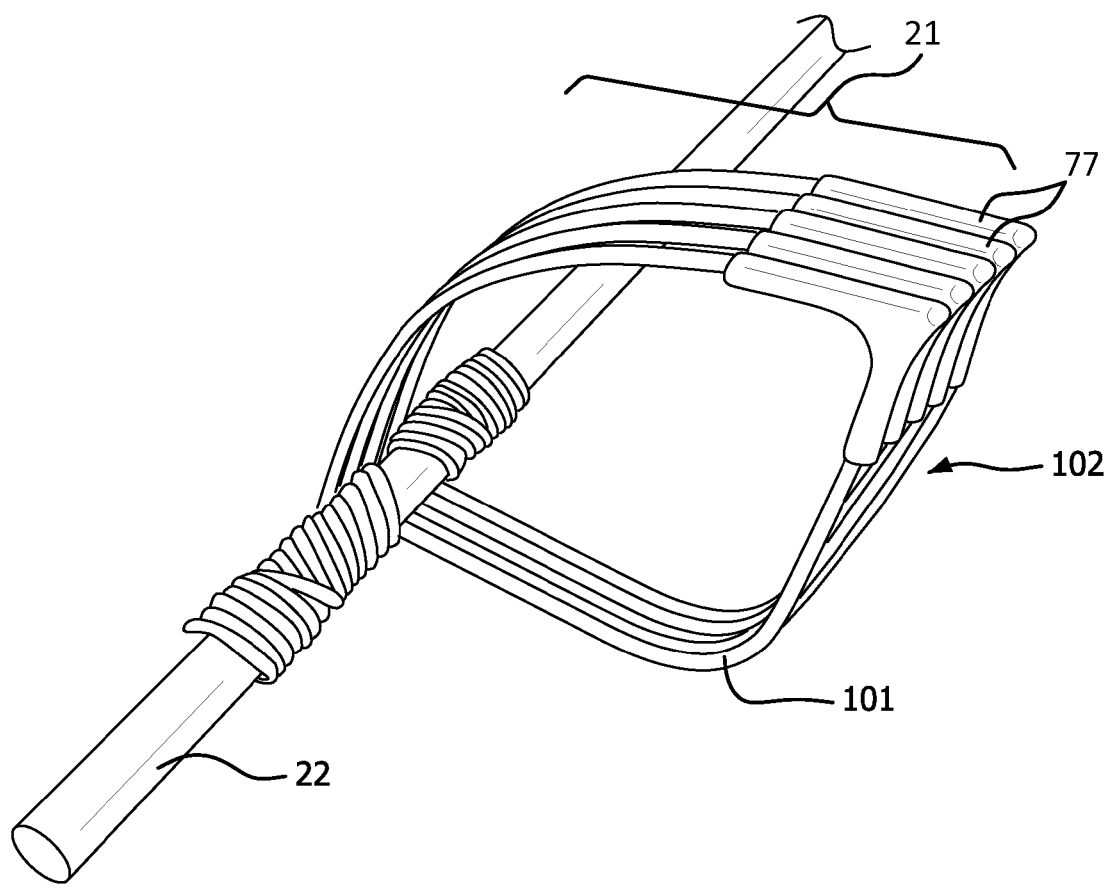
FIG. 9 is a perspective view of a portion of the frame of FIG. 3.

Referring particularly to FIGS. 8A and 8B, the base jig 8 is rotated about 360 degrees to create petals 21 (see FIG. 9) of frame 102 of the occlusive device 100. Anchors 77 may represent any of the anchors discussed herein, or may represent a different style of anchor. Referring particularly to FIG. 8C, the base jig 8 is rotated about another 720 degrees with the wires 101 placed on top of the center pin 22 in order to create the distal eyelet 112. A wire pivot 7 is inserted into a wire pivot hole 9 of the jig 8. The wires 101 are fed around the wire pivot 7 and placed under an anchor plate 11 of the base jig 8. The anchor plate 11 is secured to the base jig 8 with screws 15. The wires 101 are cut on a weighted side of the anchor plate 11.

With the weights removed, the assembly can be placed in a convection oven set to a temperature of about 475° C. for about 15 minutes, for example. The assembly can be removed from the oven and quenched in water. The jigs 8 and 38 can then be disassembled, and the partially formed occlusive device can be removed (see FIG. 9).

Referring to FIGS. 10A and 10B, the wire ends are trimmed to the eyelets 110 and 112, and petals 21 of the frame 102 are fanned in the same direction as the helical winding of the wires 101 around the eyelets 110 and 112, such that each petal 21 is offset by about 60 degrees relative to the adjacent petal 21. For implementations that use different numbers of wires 101 and petals 21, the petals 21 may be offset by other amounts. For example, for a four-wire device with four petals, each petal may be offset by about 90 degrees relative to the adjacent petal. For a five-wire device with five petals, each petal may be offset by about 72 degrees relative to the adjacent petal. For an eight-wire device with eight petals, each petal may be offset by about 45 degrees relative to the adjacent petal. As can be seen with reference to FIG. 10A, each petal 21 may overlap a portion of an adjacent petal 21.

Figure 11A:
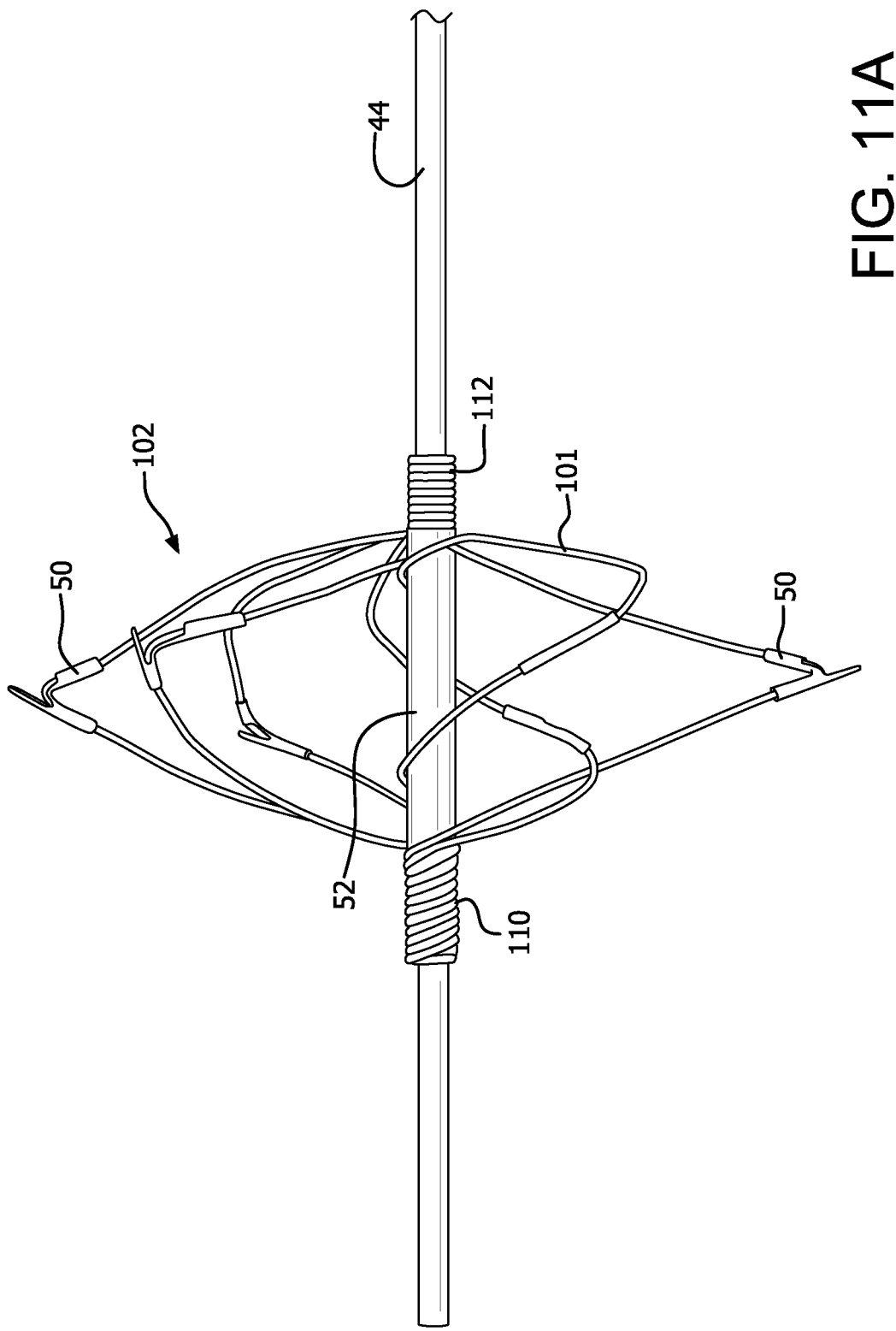
FIGS. 11A and 11B are perspective views of the frame of FIG. 3 as engaged with a heat set mandrel prior to a heat treatment.
Figure 11B:
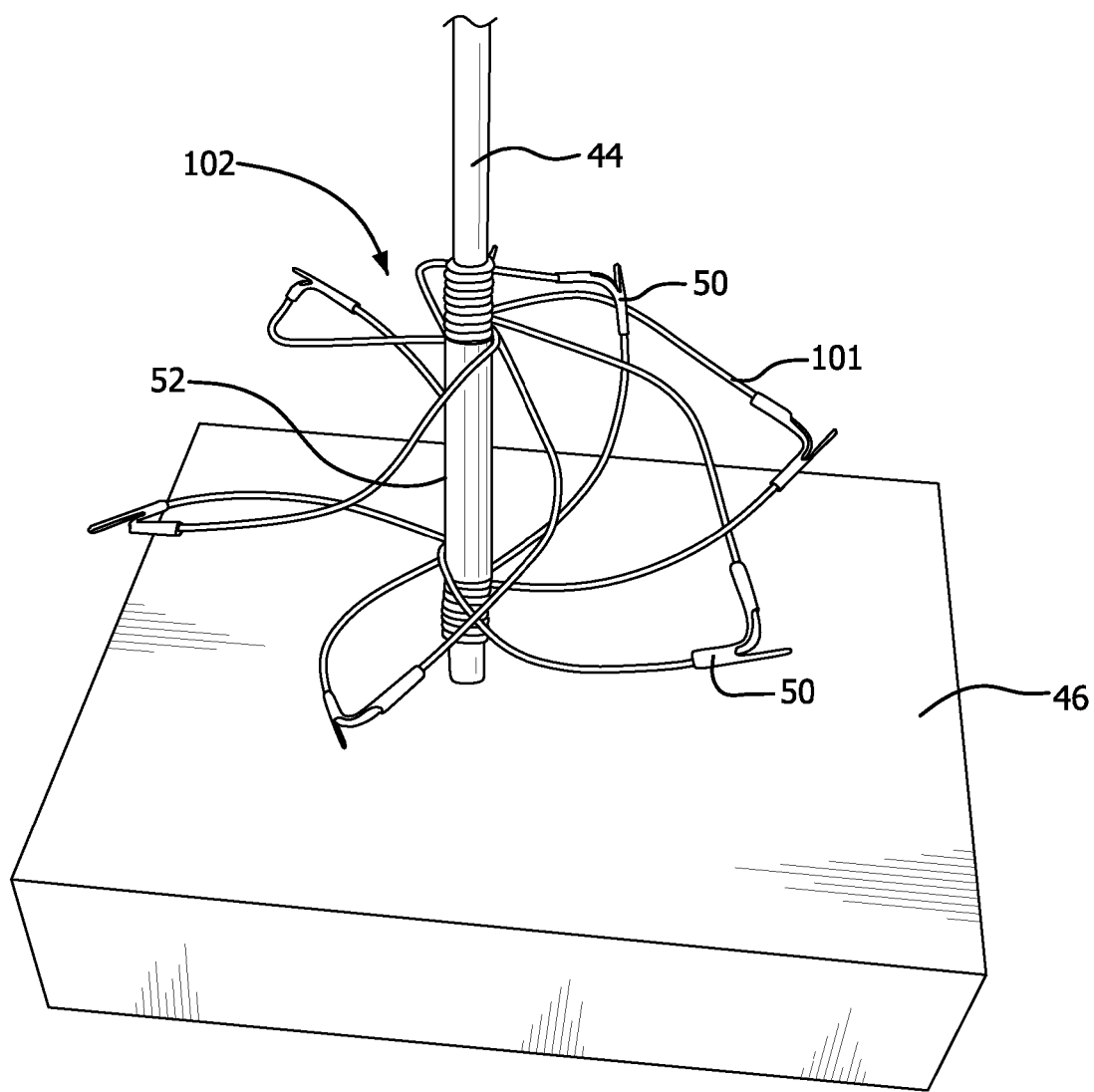
Figure 12A:
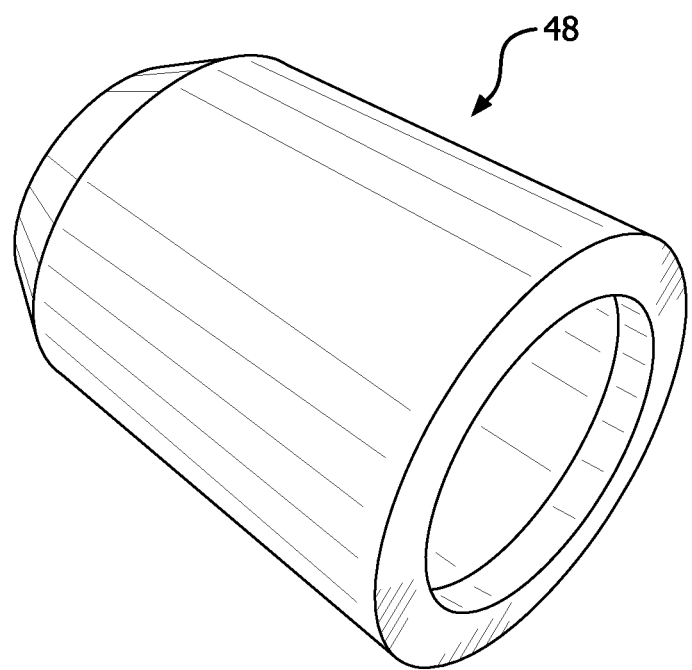
FIGS. 12A, 12B, and 12C are perspective views of a heat set tool that can be used to set the frame of FIG. 3.
Figure 12B:
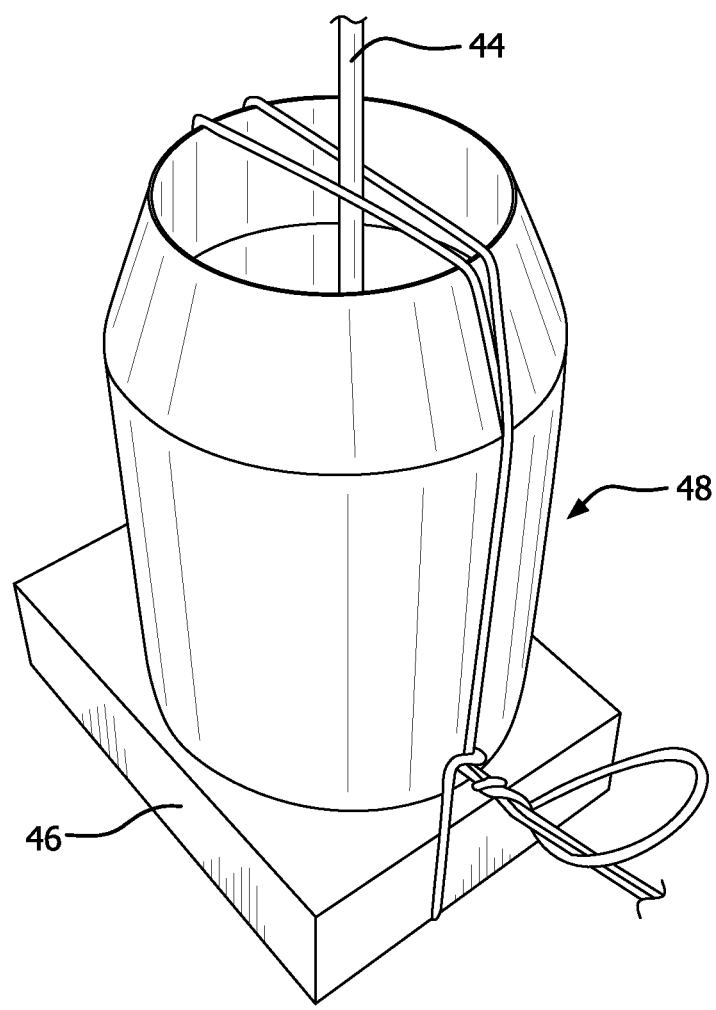
Figure 12C:
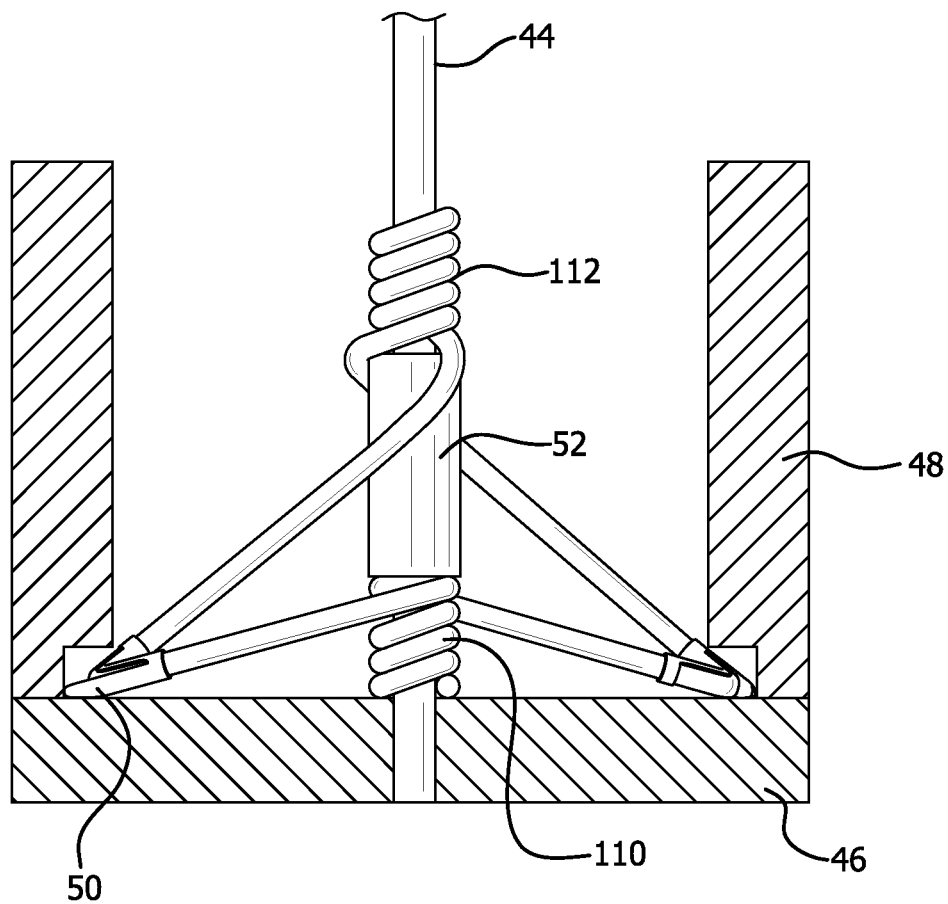

Referring to FIGS. 11A and 11B, a heat set mandrel 44 is obtained. A spacer tube 52 is placed between the eyelets 110 and 112. Referring to FIGS. 12A-12C, the heat set mandrel 44 along with the partially formed occlusive device is then placed inside of a heat set tool 48, such that the petals 21 of the device 100 are positioned inside of the heat set tool 48. The heat set mandrel 44 is inserted into a center hole of a base plate 46. The heat set tool 48 is positioned to achieve desired angles of the petals 21, and the wires 101 are bound together using a twisted tie wire. The assembly can be placed in a convection oven set to a temperature of about 475 degrees for about 15 minutes, removed, and quenched with water.

While maintaining a desired orientation of the petals 21, the partially formed occlusive device may be powder coated with a fluorinated ethylene propylene (FEP) powder in the following manner. The frame 102, spacer tube 52, and heat set mandrel 44 are inserted into a blender (e.g., the Variable Speed Lab Blender, Waring, Torrington, Conn.). One end of the heat set mandrel 44 is grounded. An amount of FEP powder is added to the blender, while leaving tips of the blender blades exposed. The frame 102, spacer tube 52, and heat set mandrel 44 are suspended in a central region of the blender, a lid is placed on the blender, and the blender is turned on to the highest setting for about 5 seconds. The frame 102, spacer 52, and the heat set mandrel 44 are removed, and the heat set mandrel 44 is tapped to achieve a more uniform powder coating on the frame 102. A slight vacuum is applied to anchoring points to remove any excess FEP powder, and the frame 102, spacer tube 52, and mandrel 44 are then hung inside a convection oven set to a temperature of about 320° C. for about 3 minutes.

Figure 13:
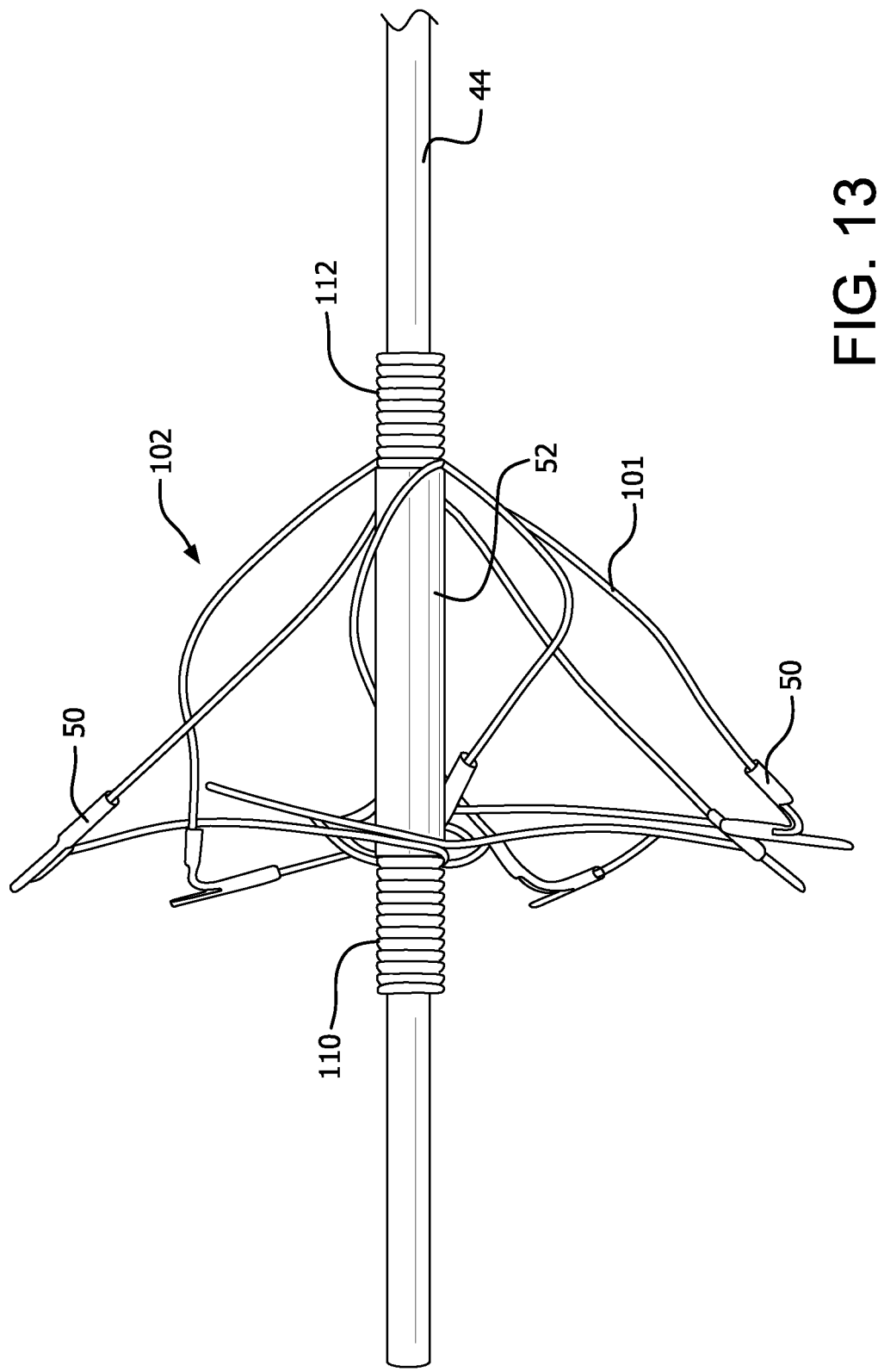
FIG. 13 is a perspective view of the frame of FIG. 3 as engaged with the heat set mandrel of FIGS. 11A and 11B and following a heat treatment.
Figure 14A:
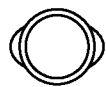
FIGS. 14A and 14B are views of an example heat set mandrel.
Figure 14B:
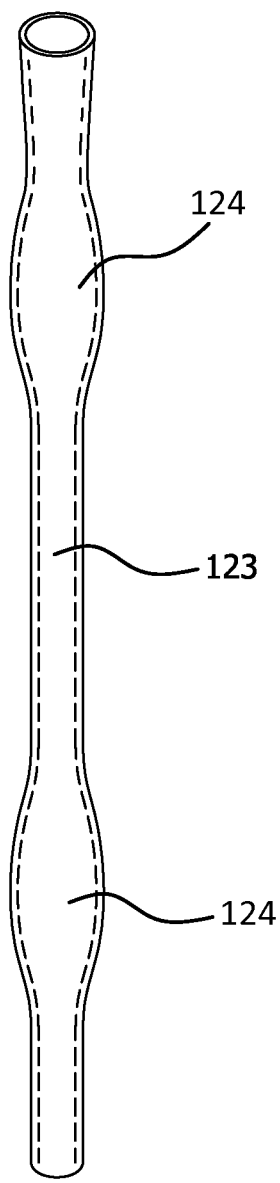

Referring now to FIG. 13, the frame 102, spacer tube 52, and heat set mandrel 44 are removed from the oven and allowed to cool. The mandrel 44 can then be extracted and spacer tube 52 can be removed from between the two eyelets 110, 112. Referring to FIGS. 14A and 14B, a crimped mandrel 123 is shown, and includes first and second crimps 124, spaced an appropriate distance from one another. The crimps may hold the eyelets apart during certain processing steps, such as powder coating and graft attach, for example. The frame 102 is extended in length on the crimped mandrel 123 by grasping the proximal and distal eyelets 110 and 112 with tweezers. The eyelets 110 and 112 are fixed at a position beyond the crimps 124 in the mandrel 123.

Membrane 104 of the occlusive device 100 may include a porous ePTFE film in some implementations. The membrane 104 may have the following properties in some implementations: a methanol bubble point of about 0.7 psi; a mass/area of about 2.43 g/m$^2$; a longitudinal matrix tensile strength of about 96,000 psi; an orthogonal matrix tensile strength of about 1,433 psi; a longitudinal maximum load of about 1.6 kg/in.; and a thickness of about 0.00889 mm. The methanol bubble point can be measured using a custom built machine that has a 1 inch diameter foot, a ramp rate of 0.2 psi/second, and a liquid media of methanol. A length and width of the material can be measured using a metal ruler. The mass/area is measured using a balance (e.g., Model GF-400 Top Loader Balance, ANG, San Jose, Calif.) with a 36×5 inch sample. The longitudinal maximum load is measured using a materials test machine (e.g., Model 5564, Instron, Grove City, Pa.) equipped with a 10 kg load cell. The gauge length is 1 inch, and the cross head speed is 25 mm/minute. The sample width is 1 inch. The longitudinal tensile test measurements are acquired in a length direction of the material. The thickness is measured using a thickness gauge (e.g., Mitutoyo Digital Indicator 547-400) with a foot diameter of ¼ inch. The longitudinal matrix tensile strengths (MTS) are calculated using the following equation:

$$\text{Matrix Tensile Strength} = \frac{(\sigma_{sample}) * (\rho_{PTFE})}{(\rho_{sample})}$$

$$\text{where: } \rho_{PTFE} = 2.2 \text{ grams/cm}^3$$

$$\sigma_{sample} = (\text{Maximum Load/Width})/\text{Thickness}$$

$$\rho_{sample} = (\text{Mass/Area})/\text{Thickness}$$

Density is calculated as mass divided by volume.

A 30 mm film tube can be constructed from the ePTFE material in the following manner. For a 25 mm diameter occlusive device, a film with a slit width of about 1.905 cm is wound on a mandrel having an outer diameter of 30 mm. A degree of film overlap may vary, but preferably there will be at least some overlap of the edges. The tube may then be removed from the mandrel and stretched until the inner diameter of the tube is about 25 mm.

The film tube may then be slipped over the tensioned article using ePTFE film, and the ends of the tube may be cinched around the two eyelets 110, 112. Another porous ePTFE film that is coated with a layer of FEP powder is obtained having the following properties, in some implementations: a mass/area of about 36.1 g/m$^2$; a longitudinal maximum load of about 12.6 kg/in.; a transverse maximum load of about 0.3 kg/in.; and a thickness of about 0.0012 in. The FEP thickness in the film is about 62.5%. FEP thickness (%) is calculated as ratio of the FEP thickness and the film thickness. The reported value represents the average measurements for five samples. FEP thickness and film thickness is measured from scanning electron microscope images of cross sections of the ePTFE/FEP laminate material in the following manner. A magnification is chosen to enable the viewing of the entire film thickness. Five lines perpendicular to the horizontal edge of the image are randomly drawn across the full thickness of the film. Thickness is determined by measuring the thickness of the FEP and the thickness of the film.

A 2 mm wide strip of the FEP-coated ePTFE film, with the FEP side down, is wrapped four times around the cinched portions and heated with a soldering iron to bond the film layers together. The occlusive device 100 (as shown in FIGS. 1 and 2) and the mandrel are placed inside a convection oven set to a temperature of about 320° C. for about 3 minutes and then removed and allowed to cool. The excess ePTFE material is trimmed.

Some of the examples described above have included embodiments of occlusive devices with separate anchor members 50 that are attached to one or more wires 101 of the device frame 102 (see, e.g., FIGS. 1, 2, 8A-C, and 9), and embodiments where bends 115 in the wires 101 of the frame 102 may themselves be used to anchor the device (see, e.g., FIGS. 3, 4A, 4B) at a delivery site. In some implementations, an occlusive device can be formed so that one or more of the wires of the occlusive device defines an anchor feature that is integrated with the device. In particular, an occlusive device can be formed so that one or more of the wires of the occlusive device defines an anchor feature that is integrated with an anchor arm of the device, and where anchor arms collectively define an anchor region of the device.

In addition to being directed to the teachings described above and claimed below, devices and/or methods having different combinations of the features described above and claimed below are contemplated. As such, the description is also directed to other devices and/or methods having any other possible combination of the dependent features claimed below.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles described herein, to the full extent indicated by the broad, general meaning of the terms in which the appended claims are expressed. To the extent that these various modifications do not depart from the spirit and scope of the appended claims, they are intended to be encompassed therein.

What is claimed is:

1. An occlusive device comprising:
 a frame element having a longitudinal axis, a distal end and a proximal end and a plurality of struts extending therebetween;
 an occlusive face having a peripheral edge and a substantially planar orientation including portions of the plurality of struts curved about the longitudinal axis and arranged non-overlapping from one another within the occlusive face, the occlusive face positioned toward the proximal end of the frame element; and
 a tapered region that extends between the distal end and the proximal end formed by other portions of the plurality of struts curved from the portions of the plurality of struts forming the occlusive face.

2. The occlusive device of claim 1, wherein the frame element comprises a delivery configuration and a deployed configuration, and the frame element is configured to collapse to the delivery configuration upon insertion into a component of a delivery system.

3. The occlusive device of claim 1, wherein the plurality of struts are configured to fan out to form occlusive features and anchoring features of the occlusive device.

4. The occlusive device of claim 3, wherein the anchoring features comprise bends in the plurality of struts of the frame element.

5. The occlusive device of claim 4, wherein the anchoring features comprise at least one anchor positioned on an exterior portion of the frame element.

6. The occlusive device of claim 5, wherein the at least one anchor is arranged and attached to a portion of the frame element in the tapered region on the frame element.

7. The occlusive device of claim 1, wherein the occlusive face is configured to conform to a shape of an ostium in a deployed configuration.

8. The occlusive device of claim 7, wherein a diameter of the occlusive face is configured to adjust during deployment of the occlusive device by transmitting torque to the frame element.

9. The occlusive device of claim 1, further comprising a proximal eyelet arranged at the proximal end, a distal eyelet arranged at the distal end, and a generally cylindrical region extending from the occlusive face in a distal direction, wherein the tapered region extends from the cylindrical region toward the distal end.

10. The occlusive device of claim 9, wherein at least one of the proximal eyelet and the distal eyelet is configured to engage one or more components of a delivery system.

11. The occlusive device of claim 1, further comprising a membrane arranged to cover the frame element.

12. The occlusive device of claim 11, wherein the membrane comprises a fluoropolymer.

13. The occlusive device of claim 11, wherein the membrane comprises polytetrafluoroethylene.

14. The occlusive device of claim 11, wherein the membrane comprises expanded polytetrafluoroethylene.

15. The occlusive device of claim 11, wherein the membrane is configured to induce rapid tissue ingrowth that occludes passage of blood through the membrane.

16. The occlusive device of claim 11, wherein the membrane is configured to serve as a tissue ingrowth scaffold for anchoring of the occlusive device.

17. The occlusive device of claim 1, wherein the frame comprises a plurality of struts.

18. The occlusive device of claim 17, wherein the plurality of struts comprise nitinol.

19. The occlusive device of claim 1, wherein the frame comprises a cylindrical region, the cylindrical region extending a first distance from the occlusive face in a generally distal direction, and the tapered region extending from a distal end of the cylindrical region to the distal end of the frame.

20. The occlusive device of claim 19, the tapered region is configured to conform to a variable taper.

21. The occlusive device of claim 1, further comprising petals that define the occlusive face.

22. A method of occluding a vessel, comprising:
 providing an occlusive device that comprises (a) a frame element having a longitudinal axis, a distal end and a proximal end and a plurality of struts extending therebetween, and a delivery configuration and a deployed configuration; (b) an occlusive face having a peripheral edge and a substantially planar orientation including portions of the plurality of struts curved about the longitudinal axis and arranged non-overlapping from one another within the occlusive face and positioned toward the proximal end of the frame element; and (c) a tapered region that extends between the distal end and the proximal end in the deployed configuration formed by other portions of the plurality of struts curved from the portions of the plurality of struts forming the occlusive face;

configuring the occlusive device in the delivery configuration and advancing the occlusive device to a delivery site; and deploying the occlusive device at the delivery site.

23. The method of claim 22, wherein the delivery site is a left atrial appendage.

24. The method of claim 23, wherein the frame element comprises a plurality of struts, and the plurality of struts are configured to fan out to form occlusive features and anchoring features of the occlusive device, and the anchoring features engage tissue near an ostium of the left atrial appendage.

* * * * *